(12) United States Patent
Tono et al.

(10) Patent No.: US 9,274,104 B2
(45) Date of Patent: Mar. 1, 2016

(54) MEASURING SYSTEM USING OPTICAL WAVEGUIDE, MEASURING DEVICE, MEASURING METHOD, OPTICAL WAVEGUIDE TYPE SENSOR CHIP, AND MAGNETIC FINE PARTICLE

(75) Inventors: Ichiro Tono, Kanagawa-ken (JP); Shingo Kasai, Kanagawa-ken (JP); Takaaki Wada, Tokyo (JP); Isao Nawata, Kanagawa-ken (JP); Masaaki Hirakawa, Kanagawa-ken (JP); Tomohiro Takase, Kanagawa-ken (JP); Kayoko Oomiya, Kanagawa-ken (JP); Takeshi Yamauchi, Kanagawa-ken (JP); Tadahiro Nakayama, Kanagawa-ken (JP); Isamu Nitta, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/436,115

(22) Filed: Mar. 30, 2012

(65) Prior Publication Data
US 2012/0252111 A1 Oct. 4, 2012

(30) Foreign Application Priority Data

Mar. 30, 2011 (JP) .................................. 2011-076412
Sep. 14, 2011 (JP) .................................. 2011-201221
Jan. 23, 2012 (JP) .................................. 2012-011456

(51) Int. Cl.
*G01N 15/06* (2006.01)
*G01N 27/00* (2006.01)
(Continued)

(52) U.S. Cl.
CPC ...... *G01N 33/54326* (2013.01); *G01N 15/0656* (2013.01); *G01N 33/5434* (2013.01); *G01N 33/54373* (2013.01); *G01N 33/585* (2013.01)

(58) Field of Classification Search
None
See application file for complete search history.

(56) References Cited

U.S. PATENT DOCUMENTS

| 2006/0045809 | A1* | 3/2006 | Shirai et al. ................. 422/82.11 |
| 2006/0068378 | A1* | 3/2006 | Mirkin et al. ..................... 435/5 |
| 2007/0059705 | A1* | 3/2007 | Lu et al. ............................ 435/6 |

(Continued)

FOREIGN PATENT DOCUMENTS

| CN | 101430328 A | 5/2009 |
| CN | 101842691 A | 9/2010 |

(Continued)

OTHER PUBLICATIONS

European Office Action issued Aug. 12, 2013 in Patent Application No. 12 162 500.8.
Partial Search Report issued Jul. 20, 2012 in European Application No. 12162500.8.

(Continued)

*Primary Examiner* — Neil N Turk
(74) *Attorney, Agent, or Firm* — Oblon, McClelland, Maier & Neustadt, L.L.P.

(57) ABSTRACT

According to one embodiment, a measuring system using an optical waveguide is provided. The measuring system has an optical waveguide, magnetic fine particles, a magnetic field applying unit, a light source and a light receiving element. The optical waveguide has a sensing area to which first substances having a property of specifically bonding to subject substances to be measured are fixed. Second substances having a property of specifically bonding to the subject substances are fixed to the magnetic fine particle. The magnetic field applying unit generates a magnetic field for moving the magnetic fine particles. The light source inputs a light into the optical waveguide. The light receiving element receives the light output from the optical waveguide.

8 Claims, 16 Drawing Sheets

(51) Int. Cl.
*G01N 33/543* (2006.01)
*G01N 33/58* (2006.01)

(56) References Cited

U.S. PATENT DOCUMENTS

| | | | |
|---|---|---|---|
| 2008/0241858 A1* | 10/2008 | Metzger et al. | ............ 435/7.2 |
| 2009/0124024 A1 | 5/2009 | Kasai et al. | |
| 2010/0092996 A1 | 4/2010 | Verschuren et al. | |
| 2011/0065209 A1 | 3/2011 | Heil et al. | |

FOREIGN PATENT DOCUMENTS

| | | | |
|---|---|---|---|
| CN | 101988922 A | 3/2011 | |
| JP | 2006-307126 A | 11/2006 | |
| JP | 2007-525651 A | 9/2007 | |
| JP | 2009-042104 | 2/2009 | |
| JP | 2009-133842 | 6/2009 | |
| JP | 2011-508199 A | 3/2011 | |
| WO | WO 2009/072457 A1 | 6/2009 | |
| WO | WO 2009/154377 A2 | 12/2009 | |
| WO | WO 2011/026030 A1 | 3/2011 | |

OTHER PUBLICATIONS

Partial European Search Report issued Sep. 25, 2014, in European Patent Application No. 14179650.8.
Office Action issued Sep. 26, 2014 in Japanese Patent Application No. 2012-011456 (with English language translation).
Japanese Office Action dated Nov. 7, 2014, issued in Japanese Patent Application No. 2011-201221 (with English translation).
Office Action mailed on Feb. 24, 2014, in Chinese patent Application No. 201210090898.7, filed on Mar. 30, 2012 (with English-Language translation).
Office Action issued Apr. 9, 2015 in Japanese Patent Application No. 2012-011456 (with English language translation).
Examination Decision of Refusal issued Mar. 13, 2015 in Japanese Patent Application No. 2011-201221 (with English language translation).
Office Action issued Sep. 29, 2015 in European Patent Application No. 14 179 650.8.
Extended European Search Report issued Jan. 26, 2015 in Patent Application No. 14179650.8.
Extended European Search Report issued Nov. 9, 2012, in European Patent Application No. 12162500.8.

* cited by examiner

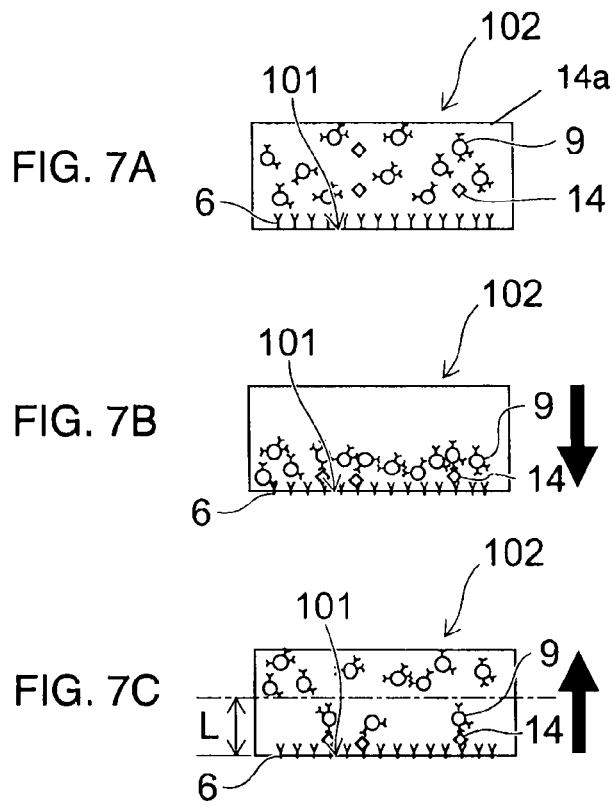
FIG. 7A
FIG. 7B
FIG. 7C
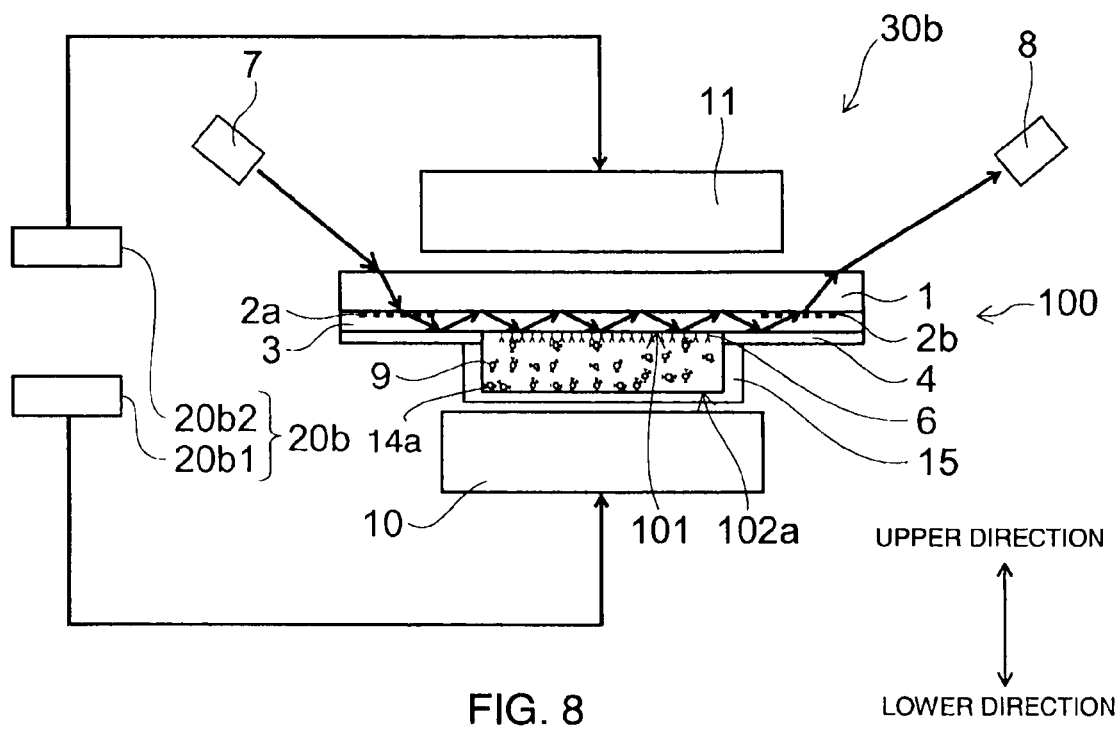
FIG. 8

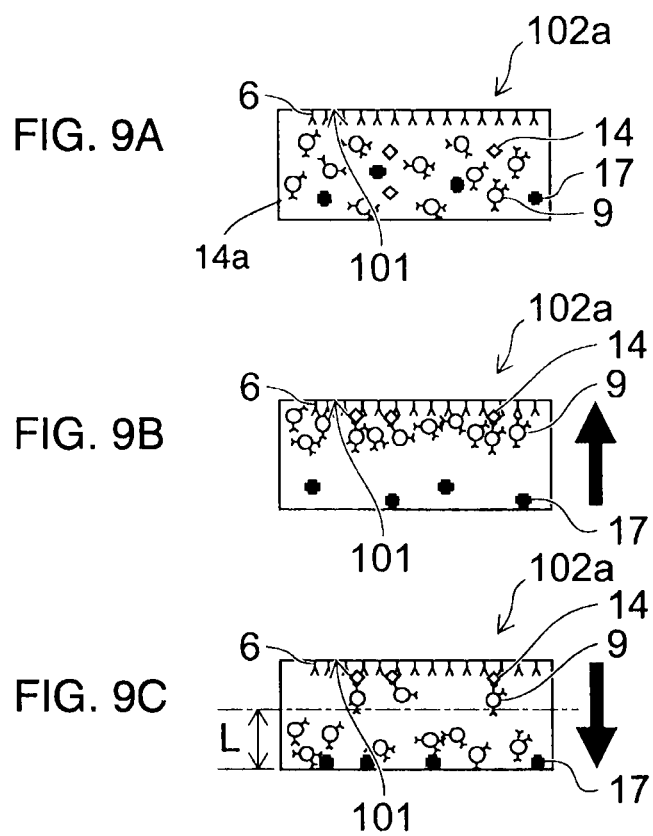

FIG. 14B1 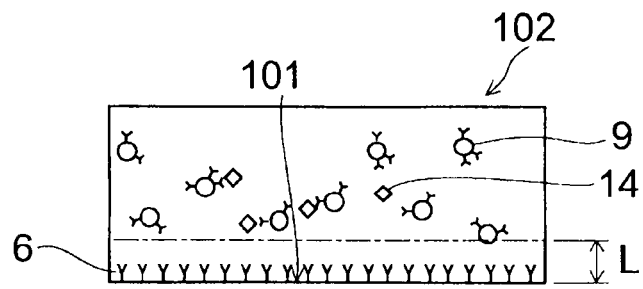
FIG. 14B2 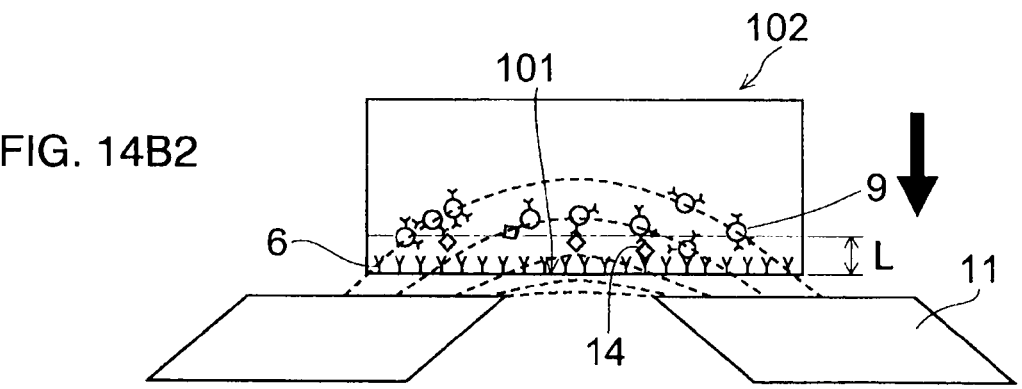

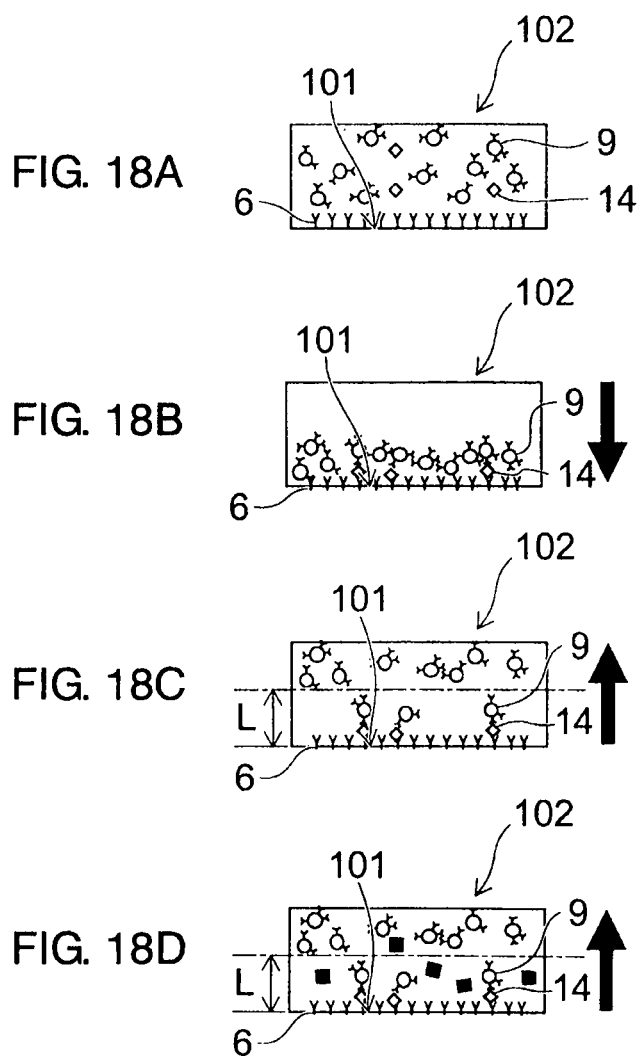

MEASURING SYSTEM USING OPTICAL WAVEGUIDE, MEASURING DEVICE, MEASURING METHOD, OPTICAL WAVEGUIDE TYPE SENSOR CHIP, AND MAGNETIC FINE PARTICLE

CROSS-REFERENCE TO RELATED APPLICATION

This application is based upon and claims the benefit of priority from the prior Japanese Patent Application No. 2011-76412, filed on Mar. 30, 2011, Japanese Patent Application No. 2011-201221, filed on Sep. 14, 2011, and Japanese Patent Application No. 2012-11456, filed on Jan. 23, 2012, the entire contents of which are incorporated herein by reference.

FIELD

Embodiments described herein relate generally to a measuring system using an optical waveguide, a measuring device using an optical waveguide, a measuring method using an optical waveguide, an optical waveguide type sensor chip, and a magnetic fine particle.

BACKGROUND

An immunoassay method which uses an antigen-antibody reaction is known. According to this method, a change in the physical amount of a light caused by a color forming reaction is measured using an evanescent wave from an optical waveguide, by employing marking bodies causing a color forming reaction and a reagent. In this method, antibodies marked with the marking bodies causing a color forming reaction are used, and each marking body corresponds to each antibody. The reaction between a pair of one antigen and one antibody produces no more than a color forming reaction caused by one marking body. Thus, the color forming amount i.e. the sensitivity of detecting subject substances to be measured has a limit, and a higher sensitivity cannot be obtained easily.

On the other hand, there is known an optical waveguide type sensor chip in which fine particles are bonded to a surface of an optical waveguide through subject substances to be measured by an antigen-antibody reaction using first and second antibodies having a property of specifically bonding to the subject substances. The first antibodies are fixed to the fine particles. The second antibodies are fixed to the optical waveguide. Since the absorbency which is caused only by the fine particles bonded to a surface of the optical waveguide by the antigen antibody reaction is detected by an evanescent light near the surface of the optical waveguide, it is possible to quantify the subject substances without a step of cleaning extra specimens or secondary antibodies.

However, the fine particles may be adhered to the surface of the optical waveguide without using an antigen-antibody reaction, and the light may be also absorbed or scattered by the fine particles which are adsorbed to the surface without using an antigen-antibody reaction. As a result, a measurement error may be caused in a measurement which needs high detection sensitivity.

In any of the above methods, development of techniques for improving the sensitivity in detection of subject substances to be measured are required for an inspection item which needs to be detected with high sensitivity.

BRIEF DESCRIPTION OF THE DRAWINGS

FIGS. 7A to 7C are diagrams illustrating steps of another method of measuring subject substances to be measured contained in a specimen solution;

FIG. 8 is a schematic diagram illustrating a configuration of a measuring system which uses an optical waveguide according to a third embodiment;

FIGS. 9A to 9C are diagrams illustrating steps of still another method of measuring subject substances to be measured contained in a specimen solution;

FIGS. 14A to 14D are diagrams illustrating steps of a method of measuring subject substances to be measured contained in a specimen solution;

FIGS. 18A to 18D are diagrams illustrating steps of still another method of measuring subject substances to be measured contained in a specimen solution;

DETAILED DESCRIPTION

Figure 1:
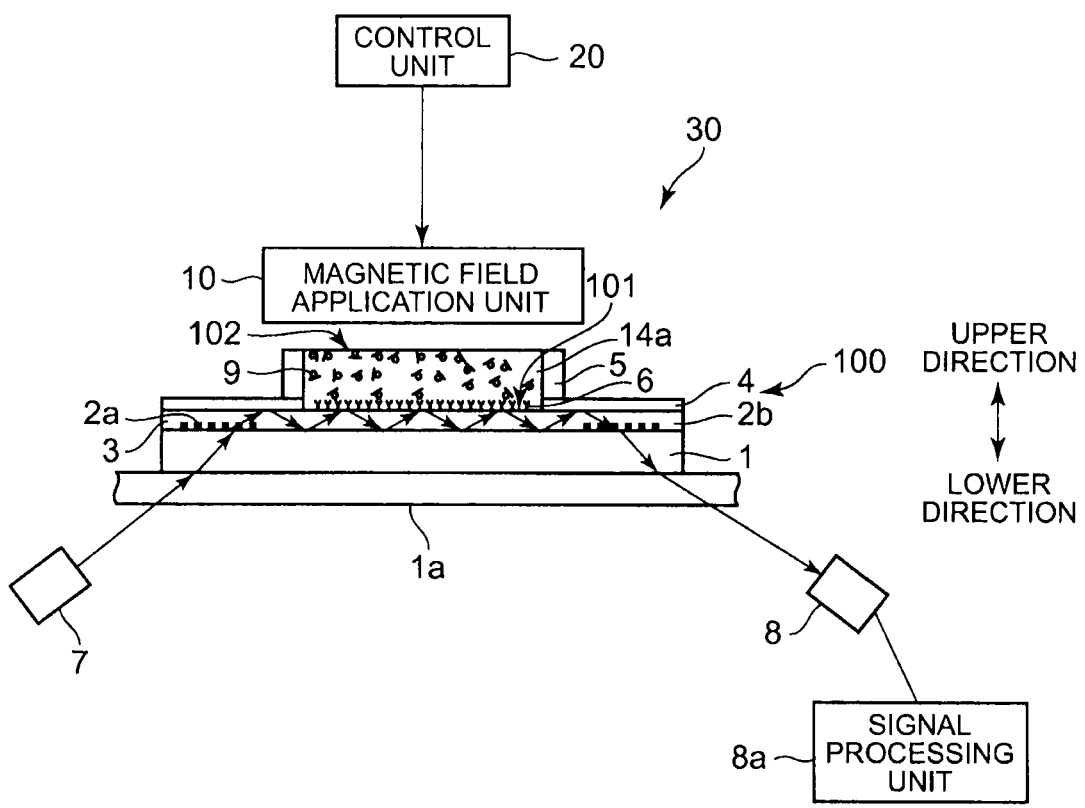
FIG. 1 is a schematic diagram illustrating a configuration of a measuring system which uses an optical waveguide according to a first embodiment.

According to one embodiment, a measuring system using an optical waveguide is provided. The measuring system has an optical waveguide, magnetic fine particles, a magnetic field applying unit, a light source and a light receiving element.

The optical waveguide has a sensing area to which first substances having a property of specifically bonding to subject substances to be measured are fixed. Second substances having a property of specifically bonding to the subject substances are fixed to the magnetic fine particles. The magnetic field applying unit generates a magnetic field for moving the magnetic fine particles. The light source inputs a light into the optical waveguide. The light receiving element receives the light output from the optical waveguide.

Hereinafter, further embodiments will be described with reference to the drawings. In the drawings, the same reference numerals denote the same or similar portions respectively.

In the description below, "above" and "upward direction" indicate a direction opposite to the direction of gravity, and "bottom" and "downward direction" indicate the direction of gravity.

FIG. 1 is a schematic diagram illustrating a configuration of a measuring system which uses an optical waveguide according to a first embodiment. A measuring system 30 according to the embodiment is provided with an optical waveguide type sensor chip 100, a light source 7, a light receiving element 8, a magnetic field applying unit 10, a signal processing unit 8a which processes an optical detection signal from the light receiving element 8, a support unit 1a which supports the sensor chip 100, and a control unit 20. The control unit 20 is provided, when needed, in order to controls magnetic field strength of a magnetic field generated by the magnetic field applying unit 10.

The optical waveguide type sensor chip 100 is provided with a substrate 1, an optical waveguide 3, a protective film 4, a frame 5, and magnetic fine particles 9. As described below, gratings 2a, 2b are provided on the substrate 1. First substances 6 which specifically react with subject substances to be measured are fixed to a surface of the optical waveguide 3. As described below, second substances which specifically react with the subject substances are fixed to the magnetic fine particles 9. The sensor chip 100 is provided with a reaction region 102 which is formed by the surface of the optical waveguide 3, an inner surface of an opening portion of the protective film 4, and an inner surface of the frame 5. A specimen solution is introduced into the reaction region 102.

The optical waveguide type sensor chip 100, the light source 7, the light receiving element 8, the magnetic field applying unit 10, and the signal processing unit 8a constitute a measuring device which uses an optical waveguide. In the case where the optical waveguide type sensor chip 100 is replaceable, the optical waveguide type sensor chip 100 is detached from the measuring device. In this case, the substrate 1 on which the optical waveguide 3 is provided may be provided on the support unit 1a.

As the optical waveguide 3, for example, a plane optical waveguide may be used. The optical waveguide 3 may be formed of, for example, a thermosetting resin such as a phenol resin, an epoxy resin, and an acrylate resin, or a light curing resin. A glass substrate itself may be used as the optical waveguide. As the material for the optical waveguide 3, a material which has permeability with respect to light to be used may be employed. A resin which has a refractive index greater than that of the substrate 1 is desirably used. The first substances 6 which specifically react with the subject substances contained in a specimen solution 14a may be fixed to a detecting surface of the optical waveguide 3, by hydrophobic interaction or chemical bonding with the sensing area 101 for example.

As the first substances 6, antibodies (primary antibodies) may be used, for example, when the subject substance contained in the specimen solution 14a are antigens.

The magnetic fine particles 9 are held on the sensing area 101 in a dispersed state, or are held on another region or a container (not illustrated). The state that the magnetic fine particles are held on the sensing area 101 in a dispersed state indicates a state where the magnetic fine particles 9 are directly or indirectly held above the sensing area 101 in a dispersed state. In this case, the state that the magnetic fine particles are indirectly held above the sensing area 101 in a dispersed state is a state where the magnetic fine particles 9 are dispersed on the surface of the sensing area 101 through a blocking layer, for example. The blocking layer may include a water-soluble substance such as polyvinyl alcohol, bovine serum albumin (BSA), polyethyleneglycol, phospholipid polymer, gelatin, casein, or sugar (for example, sucrose and trehalose).

The magnetic fine particles 9 may be disposed above the sensing area 101 with a space sandwiched between the particles 9 and the sensing area 101, in another state. For example, a support plate (not illustrated) which faces the sensing area 101 may be disposed, and the magnetic fine particles 9 may be held on a surface of the support plate facing the sensing area 101, in a dispersed state. In this case, it is desirable that the magnetic fine particles 9 are held in a dried or semi-dried state. It is desirable that the magnetic fine particles be easily dispersed again when coming into contact with a dispersing medium such as a specimen solution, but the magnetic fine particles may not necessarily be perfectly dispersed in a dried or semi-dried state. When the magnetic fine particles are held on another region or container, the magnetic fine particles may be dispersed in a dispersion liquid in a dried or semi-dried state, or may settle in a dispersing medium.

Figure 2A:
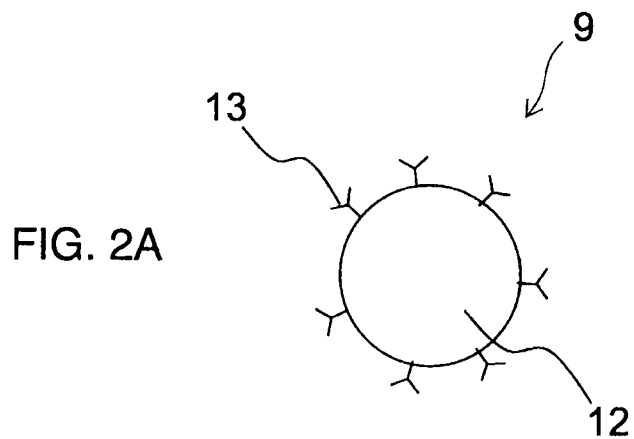
FIG. 2A is a schematic diagram illustrating an example of the magnetic fine particles.
Figure 2B:
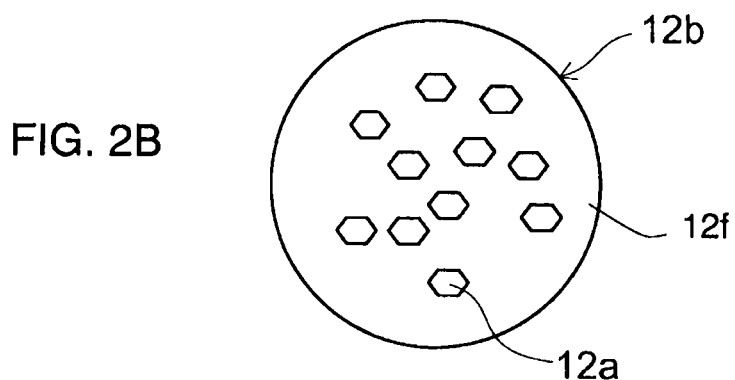
FIG. 2B is a schematic diagram illustrating a structure of a fine particle composing the example of the magnetic fine particles.
Figure 2C:
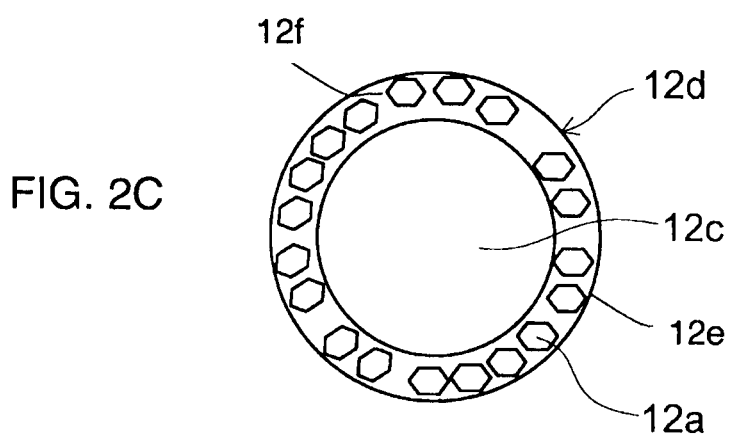
FIG. 2C is a schematic diagram illustrating another structure of a fine particle composing the example of the magnetic fine particles.

FIG. 2A is a schematic diagram illustrating an appearance of an example of the magnetic fine particles 9. FIGS. 2B and 2C are schematic diagrams illustrating cross-sections of a fine particle composing the example of the magnetic fine particles 9.

As illustrated in FIG. 2A, the respective magnetic fine particles 9 are formed so that second substances 13 are fixed to the surfaces of a fine particle 12. As the second substances 13, antibodies (secondary antibodies) may be used, for example, when the subject substances contained in the specimen solution 14a are antigens. In this case, as the fine particle 12 of FIG. 2A, a fine particle 12b shown in FIG. 2B may be used. In the fine particle 12b, magnetic nano fine particles 12a are coated with a polymer material as illustrated in FIG. 2B. As the fine particle 12 of FIG. 2A, a fine particle 12c shown in FIG. 2C may be used. In the fine particle 12c, a fine particle 12d includes a core 12c and a shell 12e for covering the core 12c as illustrated in FIG. 2C. The fine particle 12 may be a magnetic particle. In this case, it is desirable that a functional group is provided on the surface of the fine particle to bond the subject substances to the surface of the fine particle.

The core 12c may be formed of a polymer material. The shell 12e is formed of a polymer material, and may accommodate magnetic nano fine particles 12a.

Alternatively, the fine particle 12 may be a fine particle composed of a magnetic body. In this case, it is desirable that a functional group is provided on the surface of the fine particle 12 to bond the subject substances to the surfaces of the fine particle 12. As a magnetic material which is used for the fine particle 12, various kinds of ferrites such as $\gamma$-Fe2O3 may be exemplified. In this case, it is desirable to use a material which has a super-paramagnetic property in which magnetism is promptly eliminated when application of magnetic field stops.

In general, the super-paramagnetic property is a phenomenon which occurs in a nano fine particle of several tens of nano meters or less. On the other hand, the size of the fine particle needs to be several hundreds of nano meters or more so as to cause scattering of light. Accordingly, the magnetic nano fine particle 12a are appropriately coated with the material 12f such as polymer as illustrated in FIGS. 2B, 2C.

Furthermore, in general, a refractive index is mainly from about 1.5 to 1.6 in a polymer material, and is about 3.0 in ferrites. When the magnetic fine particles 9 are present near the surface of the optical waveguide 3, scattering of light becomes easier to occur as the refractive index is larger. Accordingly, it is considered that the subject substances are detected with higher sensitivity when the magnetic nano fine particles are distributed near the surfaces of the fine particles to which evanescent light is radiated.

With regard to the fine particle 12b in which the magnetic nano fine particle 12a are simply coated with a polymer material as illustrated in FIG. 2B, the magnetic nano fine particle 12a are distributed in the entire fine particle. Accordingly, from the viewpoint of detection sensitivity, as illustrated in FIG. 2C, it is appropriate that the fine particle 12d of a core shell type is used and the shell 12e contains a high density of the magnetic nano particles 12a.

The diameter of the fine particle 12 is desirably from 0.05 μm to 200 μm, and is more desirably from 0.2 μm to 20 μm. Since the light scattering efficiency is improved when using such a diameter, the detection sensitivity of the measuring system 30 which detects the subject substances using light may be improved.

The combination of the subject substances and the first substances or the second substances which is specifically bonded to the subject substances is not limited to a combination of an antigen and an antibody. A combination of sugar and lectin, a combination of a nucleotide chain and a complementary nucleotide chain, a combination of ligand and a receptor may be used.

In FIG. 1, the gratings 2a, 2b are provided on both end portions of a main surface of the substrate 1 along the main surface. The grating 2a is disposed on a light input side and the grating 2b is disposed on a light output side. The substrate 1 is formed of glass, for example. The gratings 2a, 2b are formed of a material which has a larger refractive index than that of the substrate. The optical waveguide 3 has a plane surface and are formed on the main surface of the substrate 1 on which the gratings 2a, 2b are provided.

The protective film 4 is coated on the optical waveguide 3. The protective film 4 is a resin film which has a small refractive index, for example. The protective film 4 is provided with an opening portion which is positioned between the gratings 2a, 2b and exposes a part of the surface of the optical waveguide 3. The opening portion may be formed in a rectangular shape. The sensing area 101 is a surface area of the optical waveguide 3 which is exposed to the opening portion. The frame 5 is formed on the protective film 4 so as to surround the sensing area 101. The frame 5 and the sensing area 101 of the optical waveguide 3 form a holding unit which holds the specimen solution 14a.

The first substances 6 which specifically reacts with the subject substances in the specimen solution 14a is fixed to the sensing area 101 by a hydrophobizing treatment using a silane coupling agent, for example. Alternatively, the first substance may be fixed in a manner such that functional groups are formed in the sensing area 101 and an action of appropriate linker molecules is caused to carry out chemical bonding. The second substances 13 which specifically reacts with the subject substances in the specimen solution 14a is fixed to the surface of each fine particle 12 by physical adsorption or chemical bonding through a carboxyl group, an amino group, for example.

The magnetic fine particles 9 to which the second substances 13 are fixed are dispersed directly or indirectly and held above the sensing area 101 to which the first substances 6 are fixed. The magnetic fine particles 9 may be dispersed and held in a manner such that slurry containing magnetic fine particles 9 and a water-soluble substance is coated on the sensing area 101 or on a surface (not illustrated) facing the sensing area 101 and is dried. Alternatively, the magnetic fine particles 9 may be dispersed in a liquid, and may be held in a region other than the reaction region 102 or a container (not illustrated) serving as a holding unit for a specimen solution.

The light source 7 radiates light to the sensor chip 100. The light source 7 is a laser diode emitting a red light, for example. A light which is input from the light source 7 is diffracted by the grating 2a and is propagated inside the optical waveguide 3. Subsequently, the light is diffracted by the grating 2b and is output. The light which is output from the grating 2b is received by the light receiving element 8 and the light intensity of the light is measured. The light receiving element 8 is a photo diode, for example. The amount of the magnetic fine particles 9 is measured in a manner such that the intensity of the input light is compared with the intensity of the output light to measure the absorption rate of the light. Then, the concentration of the antigens in the specimen solution 14a is obtained on the basis of the amount of the measured magnetic fine particles 9. The process in which the concentration of the antigens in the specimen solution 14a is obtained based on the amount of the measured magnetic fine particles 9 will be described in detail below.

The grating 2a is means to enter a light into the optical waveguide 3. The grating 2b is means to output a light from the optical waveguide 3. Prisms may be used to enter and output a light, instead of the gratings 2a, 2b. A light may be directly entered from one end of the optical waveguide 3, and may be directly output from the other end of the optical waveguide 3.

The magnetic field applying unit 10 applies a magnetic field to the sensor chip 100. The magnetic field applying unit 10 generates a magnetic field, and applies the generated magnetic field to the sensor chip 100 so as to move the magnetic fine particles 9 along the magnetic field. The magnetic field applying unit 10 is disposed in the direction opposite to the optical waveguide 3 seen from the magnetic fine particles 9. In the embodiment, the magnetic field applying unit 10 is arranged at a position located in an upward direction of FIG. 1. The magnetic field applying unit 10 is a magnet or an electromagnet, for example. In order to adjust the magnetic field intensity dynamically, it is desirable to use a method of adjusting the magnetic field intensity by controlling a current which flows through an electromagnet. However, the magnetic field intensity may be adjusted by selecting the intensity of a ferrite magnet itself or the distance from the sensor chip 100.

The magnetic field intensity may be adjusted in a manner such that a ferrite magnet is disposed above the sensor chip 100, a spacer is provided between the ferrite magnet and the sensor chip 100, and the thickness of the spacer is changed. Furthermore, the magnetic field intensity may be adjusted in a manner such that the relative position between the ferrite magnet and the sensor chip 100 is changed by using an actuator such as a linear motor.

In the case where an electromagnet is used, the magnetic field intensity may be adjusted in a manner such that a coil is disposed on a side opposite to a settling direction (a direction to the optical waveguide 3) seen from the magnetic fine particles 9, a current flows through the coil, and the current value is changed.

In the embodiment, since the magnetic field is applied from the magnetic field applying unit 10 to the magnetic fine particles 9, the magnetic fine particles 9 which are adsorbed to the sensing area 101 may be separated from the sensing area 101 regardless of an antigen-antibody reaction. Accordingly, it is possible to precisely measure the light absorbency caused by the magnetic fine particles 9 which are bonded to the sensing area 101 through the subject substances by an antigen-antibody reaction and to reduce measurement error.

In this case, the fine particle 12 illustrated in FIG. 2A, which constitutes an example of the magnetic fine particles 9 is desirably a fine particle having a super-paramagnetic property in which the magnetism is promptly eliminated when application of magnetic field stops. In a case where a fine particle 12 having a super-paramagnetic property is used, even when the magnetic fine particles 9 are gathered due to magnetism arising when a magnetic field is applied to the magnetic fine particles, the magnetic fine particles 9 may be dispersed again by stopping the application of the magnetic field. For example, a case where aggregations of the magnetic fine particles 9 are produced and the magnetic fine particles 9 are hardly separated from the sensing area 101 may occur, even when any subject substance does not exist in the specimen solution 14a and a magnetic field is applied to the magnetic fine particles. Such aggregations of the magnetic fine particles 9 cause measurement error. In this case, when the fine particle 12 is provided to have a super-paramagnetic property, the magnetic fine particles 9 may be suppressed from being gathered so that measurement error is suppressed.

In order to further improve re-dispersion property of the magnetic fine particles when application of magnetic field to the magnetic fine particles stops, the surfaces of the fine particle 12 may be charged to positive or negative charges. Alternatively, a dispersing agent such as a surface acting agent may be added to a dispersing medium of the magnetic fine particles 9.

Furthermore, in the embodiment, the magnetic fine particles 9 settled naturally may be returned in the upward direction by the magnetic field applying unit 10. The specimen solution 14a and the magnetic fine particles 9 may be mixed by the repeated process in which the magnetic fine particles 9 are naturally settled and are returned in the upward direction using the magnetic field applying unit 10. Accordingly, a bonding, which uses an antigen-antibody reaction of the magnetic fine particles 9 and the sensing area 101 through the antigens (the subject substances) contained in the specimen solution 14a, may be promoted, and the higher detection sensitivity may be obtained in a shorter time. Accordingly, even when subject substances are present at a low concentration, the detection sensitivity may be higher.

When the surface of the fine particle 12 of FIG. 2A are made to have positive or negative charges, or a dispersing agent such as a surface acting agent is added the surface, the magnetic fine particles 9 may be easily dispersed again when application of magnetic field stops and mixing may be further promoted. Accordingly, the detection sensitivity may become further higher.

Figure 3A:
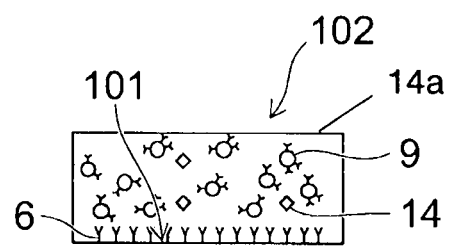
FIGS. 3A to 3C are diagrams illustrating steps of a method of measuring subject substances to be measured contained in a specimen solution.
Figure 3B:
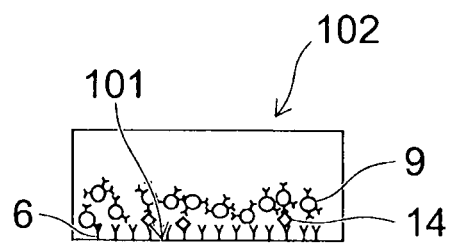
Figure 3C:
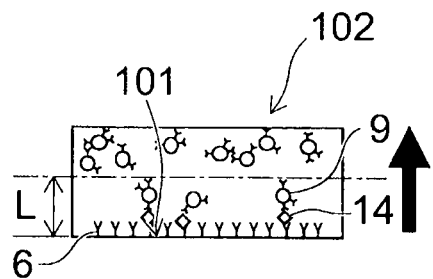

FIGS. 3A to 3C are diagrams illustrating steps of a method of measuring subject substances to be measured which are contained in a specimen solution. In this method, the amount of the subject substances is measured using the above measuring system 30. FIGS. 3A to 3C illustrate a state of the reaction region 102 respectively.

The measuring system 30 illustrated in FIG. 1 is prepared. Subsequently, as illustrated in FIG. 3A, a specimen solution is introduced into a region on the optical waveguide 3 where the magnetic fine particles 9 are dispersed and held, and the introduced magnetic fine particles 9 are dispersed again. When the magnetic fine particles 9 are held in a region other than the region on the optical waveguide 3, or in a separate container or the like, a mixture dispersion liquid of the specimen solution and the magnetic fine particles 9 may be introduced. Alternatively, the dispersion liquid of the magnetic fine particles 9 and the specimen solution may be separately introduced in a manner such that the dispersion liquid of the magnetic fine particles 9 is introduced and the specimen solution is introduced so as to mix the liquids. Such an introduction method may be performed by dripping or inflowing, for example.

It is sufficient that the specimen solution 14a including the subject substances 14, and the magnetic fine particles 9 having a magnetic property to which second substances 13 having a property of specifically bonding to the subject substances are fixed come into contact with the sensing area 101 which is provided in the sensor chip 30 and to which first substances 6 having a property of specifically bonding to the subject substances are fixed.

Subsequently, as illustrated in FIG. 3B, the magnetic fine particles 9 settle toward the sensing area 101 by their own weight at this time, the first substances 6, for example, primary antibodies fixed to the sensing area 101 and the second substances 13, for example, secondary antibodies fixed to the surface of the fine particle 12 of each of the magnetic fine particles 9 are bonded to each other through the subject substances, for example, antigens, by an antigen-antibody reaction. By this reaction, the magnetic fine particles 9 are bonded to the sensing area 101.

Furthermore, as illustrated in FIG. 3C, when a magnetic field is applied in a direction indicated by an arrow from a direction (for example, an upward direction) different from the settling direction when seen from the magnetic fine particles 9, the magnetic fine particles 9 which are absorbed to the sensing area 101 without using the subject substances can be moved in a direction different from the settling direction, for example, the upward direction, so as to be eliminated from the sensing area 101.

At this time, since the magnetic field intensity is appropriately set, the magnetic fine particles 9 which are bonded to the sensing area 101 through the subject substances 14 by the antigen-antibody reaction are not moved, and the magnetic fine particles 9 which are absorbed to the sensing area 101 without using the subject substances 14 can be eliminated.

In the embodiment, it is considered that appropriate magnetic field intensity is obtained. The state of the magnetic fine particles 9 which can be detected by near-field light such as evanescent light may be classified as the "state 1" to the "state 3" described below in accordance with difference in strength of interaction with the sensing area 101. Such classification will be described according to an order from a strong interaction to a weak interaction.

The "state 1" indicates a state of the magnetic fine particles which are bonded to the sensing area 101 according to bonding of the subject substances with molecules which are specifically bonded to the subject substances by antigen-antibody bonding. The "state 2" indicates a state of the magnetic fine particles which are non-specifically absorbed to the sensing area 101 due to a force between molecules or a hydrophobic interaction. The "state 3" indicates a state of the magnetic fine particles which float near the sensing area 101.

The magnetic fine particles of the "state 1" are those which are to contribute to detection of a concentration of the subject substances. The magnetic fine particles of the "state 2" or the "state 3" are those which may cause measuring error or noise. The magnetic fine particles which are in the "state 1" may be referred to as magnetic fine particles which are bonded to the sensing area 101. The magnetic fine particles which are in the "state 2" can be referred to as magnetic fine particles which are absorbed to the sensing area 101.

In the case of using evanescent light which comes out from a propagating medium when the light is propagated inside the optical wave guide 4 by total reflection, for example, the "near surface region" of the optical waveguide 3 where the magnetic fine particles can be detected by the near-field light may be defined by a distance d to which the evanescent light comes out.

In this case, the coming-out distance d is obtained by the following equation (1). From the equation (1), it is understood that the coming-out distance d is approximately a fraction of a wavelength of a light which is used for the measurement. A indicates the wavelength of the light used for the measurement, $n_1$ indicates a refractive index of the optical waveguide 3, $n_2$ indicates a refractive index of the dispersing medium dispersing the magnetic fine particles 9, and θ indicates a total reflection angle.

$$d = \lambda / \{2\pi(n_1^2 \sin^2\theta - n_2^2)^{1/2}\} \quad (1)$$

The magnetic field applying unit 10 applies a magnetic field having a magnetic field intensity by which the magnetic fine particles are separated from the sensing area 101 by a distance L satisfying the following equation (2), in order to avoid detection of the magnetic fine particles of the "state 2" or the "state 3".

$$L > \lambda / \{2\pi(n_1^2 \sin^2\theta - n_2^2)^{1/2}\} \quad (2)$$

For example, when λ=635 nm, $n_1$=1.58, $n_2$=1.33 (in a case where the dispersing medium is water), and θ=78°, L>130 nm. When the magnetic fine particles 9 of the "state 2" or the "state 3" are separated from the sensing area 101 to an extent of a distance as small as several hundreds of nano meters by application of magnetic field to the magnetic fine particles 9, the measurement error can be sufficiently reduced. It may take only a short amount of time to move the magnetic fine particles 9 of the "state 2" or the "state 3" to separate from the sensing area 101, in order to prevent the error of detection sensitivity.

Even though a certain time is needed, so far as the time is within an allowable range, the magnetic fine particles 9 of the "state 2" or the "state 3" can be moved by a distance which does not cause measurement error of the magnetic fine particles 9, using a smaller magnetic field intensity. By this method, it is possible to reduce a possibility that the magnetic fine particles 9 of the "state 1" which are necessary for the measurement can be further separated from the sensing area. In other words, it is possible to move the magnetic fine particles of the "state 2" or the "state 3" which may cause noise in the measurement from the sensing area 101 to an extent of a distance where the magnetic fine particles do not affect the measurement, without separating the magnetic fine particles 9 of the "state 1" which are to contribute to the measurement, from the sensing area 101. As a result, the S/N ratio can be improved.

The appropriate magnetic field intensity indicates an intensity which is appropriately used when the magnetic fine particles 9 of the "state 2" or the "state 3" which may cause noise in the measurement are moved from the sensing area 101 to an extent of a distance where the magnetic fine particles do not affect the measurement without separating the magnetic fine particles 9 of the "state 1" which contribute to the measurement from the sensing area 101. As described above, it is desirable that an electromagnet is used as the magnetic field applying unit 10 and the current is controlled so as to optimally adjust a magnetic field intensity of the electromagnet. However, a ferrite magnet or the like may be used as the magnetic field applying unit 10 and the intensity of the magnetic field of the magnet or the relative position between the sensor chip 100 and the magnet may be changed so as to adjust the magnetic field intensity. When the electromagnet is used, a coil is disposed at the opposite side of the settling direction (the direction toward the optical waveguide 3) when seen from the magnetic fine particles 9 and a current is applied to the coil. Then, the current value may be changed so as to adjust the magnetic field intensity.

In order to adjust the magnetic field intensity optimally, the measuring system 30 of the embodiment may include control unit 20 which controls the magnetic field intensity of the electromagnet to be applied from the magnetic field applying unit 10, as illustrated in FIG. 1. When the magnetic field intensity does not need to be controlled, the control unit 20 is not necessary. When the above control is performed by the control unit 20, the magnetic field intensity may be adjusted to be an appropriate intensity. For example, the magnetic field intensity may be adjusted so that the magnetic fine particles of the "state 2" or the "state 3" which can cause noise in a measurement can be separated from the sensing area 101 to an extent of a distance where the magnetic fine particles do not affect the measurement without moving the magnetic fine particles 9 of the "state 1" which are to contribute to the measurement from the sensing area 101. When the magnetic field intensity can be adjusted successively, the magnetic field intensity can be dynamically controlled by the control unit 20. For example, it is possible to control at least one of timing and a time period at which a magnetic field is applied from the magnetic field applying unit 10 to the magnetic fine particles, using the control unit 20.

A difference in intensity between optical detection signals from the light receiving element 8, which will be defined in detail below, is measured so that the amount of the subject substances 14 contained in the specimen solution 14a, for example, a concentration of the antigens can be measured. For the measurement, in FIG. 1, a laser light from the light source 7 is input from the grating 2a into the optical waveguide 3, and is propagated inside the optical waveguide 3 so as to generate near-field light such as evanescent light near the surface (an exposure surface of the sensing area 101). In this state, when a mixture dispersion liquid of the specimen solution 14a and the magnetic fine particles 9 are introduced into the sensing area 101 as illustrated in FIG. 3A, the magnetic fine particles 9 immediately settle and reach a region where the evanescent light is present near the sensing area 101 as illustrated in FIG. 3B. Since the magnetic fine particles 9 contribute to absorbing or scattering of the evanescent light, an intensity of a reflected light is attenuated. As a result, when a laser light which is output from the grating 2b is received by the light receiving element 8, the intensity of the output laser light decreases with elapse of time due to influence of the magnetic fine particles 9 bonded to the first substances 6.

Subsequently, when the magnetic field is applied in an upward direction by the magnetic field applying unit 10, as shown in FIG. 3C, the magnetic particles 9 of the "state 2" or the "state 3" move to outside of a region where the evanescent light comes out. As a result, intensity of the received light is recovered to a predetermined value. The intensity of the received light at this time is compared with intensity in the state illustrated in FIG. 3A that is a state immediately after introduction of the mixture dispersion liquid. The intensity can be numerically shown as a light intensity reduction rate. The intensity of the light which is output from the sensor chip 100 is measured before application of the magnetic field after the specimen solution is introduced into the sensor chip 100. Furthermore, the intensity of the light which is output from the sensor chip 100 is measured after the magnetic field is applied. The subject substances 14 can be quantified based on a difference in light intensity. Such measurement is performed by the signal processing unit 8a which processes an optical detection signal from the light receiving element 8.

The light intensity reduction rate of the laser light is received by the light receiving element 8 is dependent on the amount of the magnetic fine particles 9 which are bonded to the sensing area 101 mainly by an antigen-antibody reaction. The laser light intensity reduction rate is proportional to a concentration of antigens contained in a specimen solution which contribute to an antigen-antibody reaction. A curve, which indicates a change in intensity with elapse of time in a case of using a specimen solution having a known concentration of antigen, is obtained. Further, a light intensity reduction rate at a predetermined time after application of a magnetic field in the upward direction is obtained from the curve indicating the change. Then, a calibration curve indicating a relation between a concentration of antigens and the light intensity reduction rate is created. With regard to a specimen solution having an unknown concentration of antigens, the light intensity reduction rate at a predetermined time is obtained from a time measured according to the above method and the curve indicating the intensity change. The light intensity reduction rate is compared with the calibration curve so as to measure the concentration of the antigens contained in the specimen solution.

Hereinafter, an experimental example of a measurement according to the embodiment will be described. The specific numerical values or materials shown below are merely examples, and the embodiment is not limited to those numerical values or materials.

In the experiment, a titanium oxide film having a refractive index of 2.2 to 2.4 was formed to have a thickness of 50 nm by sputtering on a substrate 1 of alkali-free glass. The substrate 1 was transparent. The gratings 2a and 2b were formed by lithography and dry-etching. A UV-curable acrylate resin film having a thickness of 10 μm was formed to obtain an optical waveguide 3 by spin-coating and UV-irradiation on the substrate 1 on which the gratings 2a and 2b are provided. The refractive index after the acrylate resin film was hardened was set to 1.58.

A protective film 4 serving as a low refractive resin film was formed by screen-printing on an upper surface of the optical waveguide 3 including an upper surface area above the gratings 2a, 2b, so as to surround an antibody fixing area which is a sensing area 101. The refractive index of the protective film 4 after coating and drying was set to 1.34. In order to form a liquid storage portion for holding the specimen solution, a resinous frame 5 was fixed to the protective film 4 by a double sided tape. In the optical waveguide 3, first substances 6 having a property of bonding to subject substances to be measured were fixed to a surface of the sensing area 101 which was provided between the gratings 2a, 2b and on which any portion of the protective film was not formed, according to a covalent binding method.

In the embodiment, rat insulin was used as the subject substances, and anti-rat insulin antibodies were used as the first substances 6 fixed to the sensing area 101. A core shell type fine particle 12d illustrated in FIG. 2C was used as an example of the magnetic fine particles 9. Each fine particle 12d accommodates magnetic nano fine particles 12a in a shell 12e highly densely. The mean diameter of each fine particle 12d was set to 1.1 gm. Anti-rat insulin antibodies as second substances 13 were fixed to the surface of each fine particle 12d by a covalent binding method. A dispersion liquid which includes the magnetic fine particles 9 obtained in this way was prepared.

Subsequently, a light having a central wavelength of 635 nm of the light emitting diode 7 was input from the grating 2a, and the light intensity of the light output from the grating 2b was detected by the photo diode 8. While detecting the output light, a specimen solution 14a and the dispersion liquid of the magnetic fine particles 9 were mixed, and the obtained mixture liquid was introduced into the sensing area 101 surrounded by the frame 5. Subsequently, according to the above measurement sequence, the light intensity of the light output from the grating 2b was measured.

In this experiment, a ferrite magnet was used as the magnetic field applying unit 10And the magnet was disposed above the sensor chip 100. A spacer was provided between the magnet and the sensor chip 100, and the thickness of the spacer was changed so that the magnetic field intensity could be changed.

Figure 4:
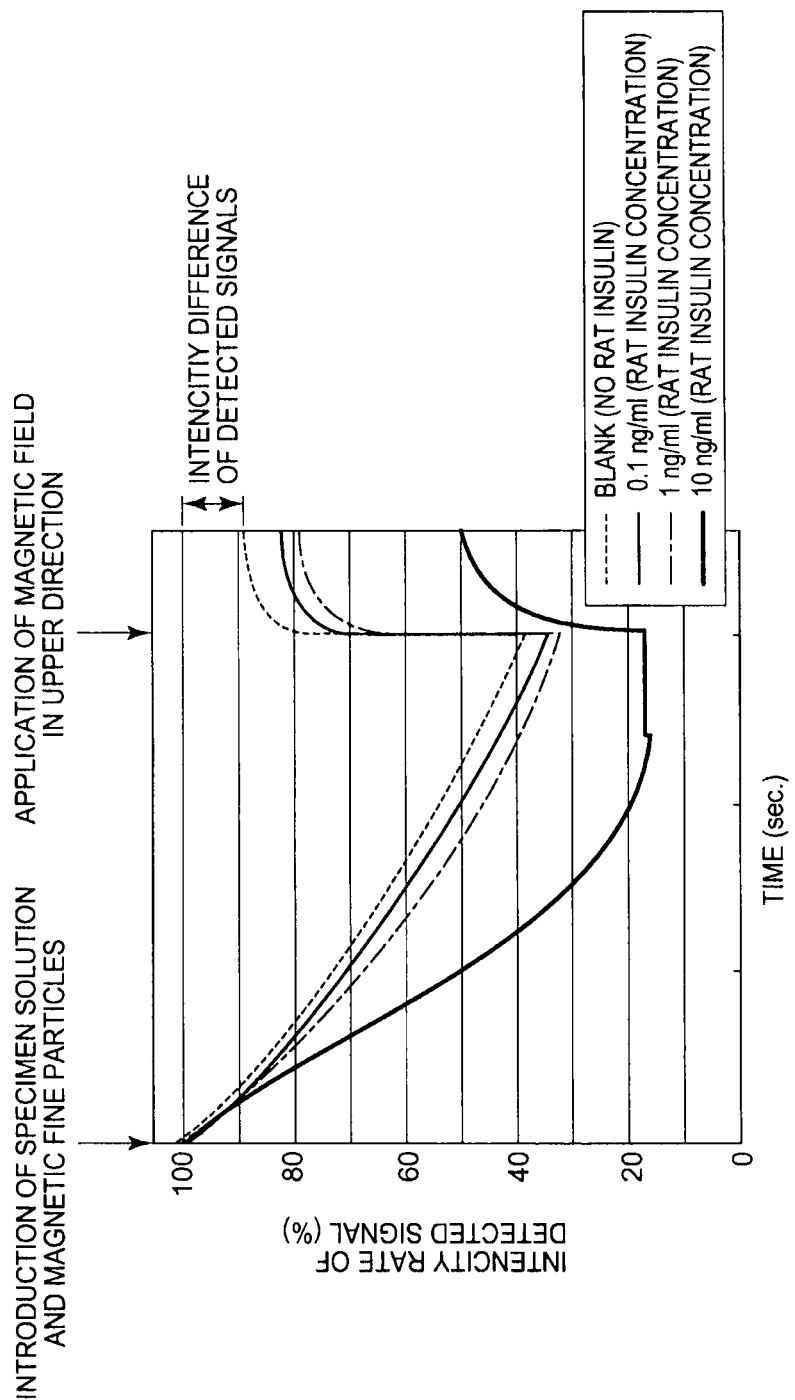
FIG. 4 is a diagram illustrating an example of a change over time in intensity ratio of an optical detection signal which is measured by the method.
Figure 5:
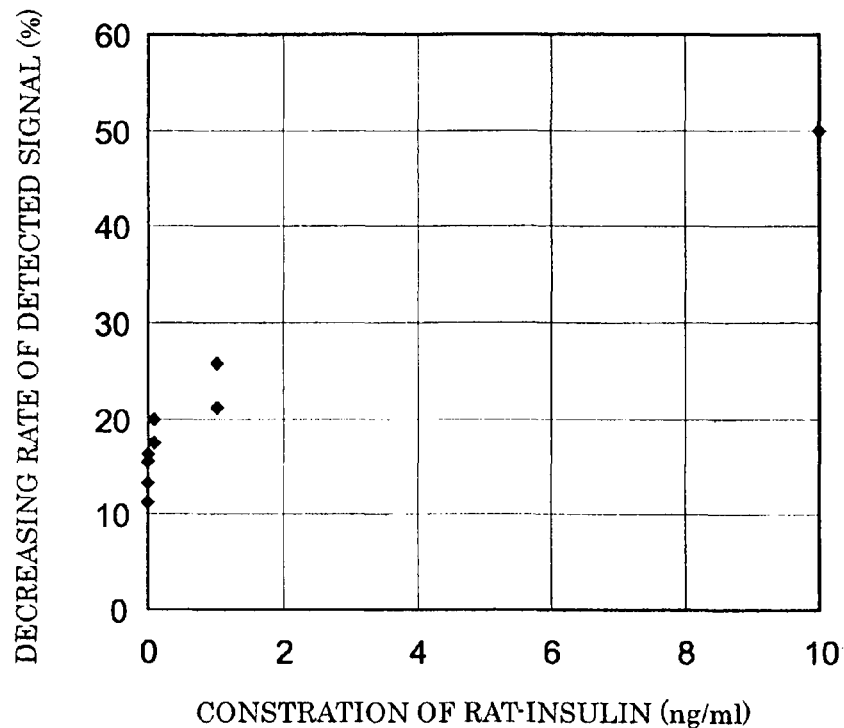
FIG. 5 is a diagram illustrating a calibration curve of a measurement result according to the method.

FIG. 4 is a diagram illustrating an example of a change over time in a signal intensity ratio of the optical detection which is measured by the above method. FIG. 5 is a diagram illustrating a calibration curve of a measurement result according to the above method.

As illustrated in FIG. 4, when the dispersion liquid of the magnetic fine particles 9 and the specimen solution are mixed and the mixture liquid is introduced into the sensing area 101, the signal intensity ratio of the optical detection reduces in accordance with increase in a density of the fine particles near the sensing area 101 due to settling of the magnetic fine particles 9. Subsequently, a magnetic field is applied by the magnetic field applying unit 10. With application of the magnetic field, the magnetic fine particles 9 which can cause noise in the measurement and are absorbed to the sensing area 101 are eliminated. As a result, the intensity ratio of the detected signal increases again, and is saturated at a value which is lower than an initial intensity ratio of the detected signal. The difference between the intensity ratio at this stage and the initial intensity ratio is defined as a ratio with respect to the initial intensity ratio, that is, a signal reduction rate. The calibration curve illustrated in FIG. 5 indicates a relation between the signal reduction rate and the rat insulin concentration.

From FIGS. 4 and 5, using the above measuring method, the following were found. The magnetic fine particles 9, which are caused to be absorbed to the sensing area 101 by a non-specific absorption and can cause a measurement error as noises, are eliminated from a region where an evanescent wave is present under application of an appropriate magnetic field. As a result, even an extremely low concentration of rat insulin can be detected.

According to the measuring system of the embodiment, since the magnetic field is applied to the magnetic fine particles 9 in a direction different from the settling direction, the magnetic fine particles 9 which are absorbed to the sensing area 101 without an antigen-antibody reaction and may cause noise can be separated from the sensing area 101. Accordingly, it is possible to precisely measure the absorbency caused by the magnetic fine particles 9 which are bonded to the sensing area 101 through the subject substances 14 by the antigen-antibody reaction, and to reduce the measurement error.

In addition, when the magnetic fine particles 9 which can cause noises can be eliminated by application of the magnetic field, such magnetic fine particles do not need to be eliminated by cleaning.

According to the embodiment, since the optical waveguide type sensor chip 100 is used and the measurement is performed using near-field light such as evanescent light, a distance, which is necessary for moving the magnetic fine particles 9 to the extent that the measurement from the sensing area 101 is not affected, can be short. Accordingly, a time period, which is necessary for moving the magnetic fine particles 9 from the sensing area 101 by the application of the magnetic field in the upward direction, can be short. Alternatively, the magnetic fine particles 9 can be moved to the extent that the measurement from the sensing area 101 is not affected by a magnetic field having a smaller intensity.

According to the embodiment, since the magnetic field intensity can be controlled, it is possible to move and separate the magnetic fine particles 9 which can cause noises in the measurement from the sensing area 101 up to a distance where the measurement is not affected, without moving the magnetic fine particles 9 which are to contribute to the measurement from the sensing area 101. Accordingly, the S/N ratio can be better.

According to the embodiment, the magnetic field intensity of the magnetic field applying unit 10 can be dynamically controlled by a control unit 20, and the measurement precision can be highly maintained by the control unit 20.

In a case where fine particles having a super-paramagnetic property in which the magnetism is promptly eliminated when application of a magnetic field stops are used for each fine particle 12 of the magnetic fine particles 9 as illustrated in FIG. 2A, the magnetic fine particles 9 can be easily dispersed again when the application of the magnetic field stops. Accordingly, even when the subject substances are not present in the specimen solution, aggregation of the magnetic fine particles 9 is suppressed from being generated so that occurrence of measurement error can be suppressed. In a case where the core shell type fine particle 12d accommodating the magnetic nano fine particles 12a in the shell 12e as illustrated in FIG. 2C are used as the magnetic fine particles 9, the scattering intensity of evanescent light can be increased. As a result, the subject substances can be detected sensitively.

In a case where the surface of the fine particle 12 of each magnetic fine particle 9 is made to have positive or negative charges, or a dispersing agent such as a surface acting agent is added onto the surface, the magnetic fine particles 9 can be easily dispersed again when application of magnetic field stops, and the measurement error can be reduced.

According to the embodiment, the magnetic fine particles 9 naturally settled can be returned by the application of the magnetic field in the direction different from the settling direction. Since the specimen solution and the magnetic fine particles 9 are mixed by the repeated process in which the magnetic fine particles 9 are naturally settled and are returned in the upward direction using the magnetic field applying unit 10, the antigen-antibody reaction between the subject substances 14 contained in the specimen solution, the antigen, for example, and the magnetic fine particles 9 is promoted, and a high sensitivity detection can be attained in a shorter time. Accordingly, even when the subject substances 14 are present at a low concentration, the detection sensitivity can be better.

In a case where the surface of each fine particle 12 in the respective magnetic fine particles 9 is made to have positive or negative charges, or when a dispersing agent such as a surface acting agent is added onto the surface, the magnetic fine particles 9 can be easily dispersed again when application of magnetic field stops, the mixing can be promoted, and the detection sensitivity can be better.

According to the embodiment, the optical waveguide type sensor chip 100 is used, and the amount or the concentration of the subject substances 14 can be measured by near-field light such as evanescent light. In this case, when the magnetic fine particles 9 each having a diameter of 0.05 µm or more and 200 µm or less, or desirably 0.2 µm or more and 20 µm or less are used, the light scattering efficiency can be better so that the sensitivity in detection of the subject substances 14 can be better.

In the first embodiment, the magnetic field is applied in the direction opposite to the optical waveguide 3 when seen from the magnetic fine particles 9. But, in a second embodiment, a magnetic field can be applied in both of a direction toward the optical waveguide 3 and a direction opposite to the optical waveguide 3 when seen from the magnetic fine particles 9.

Figure 6:
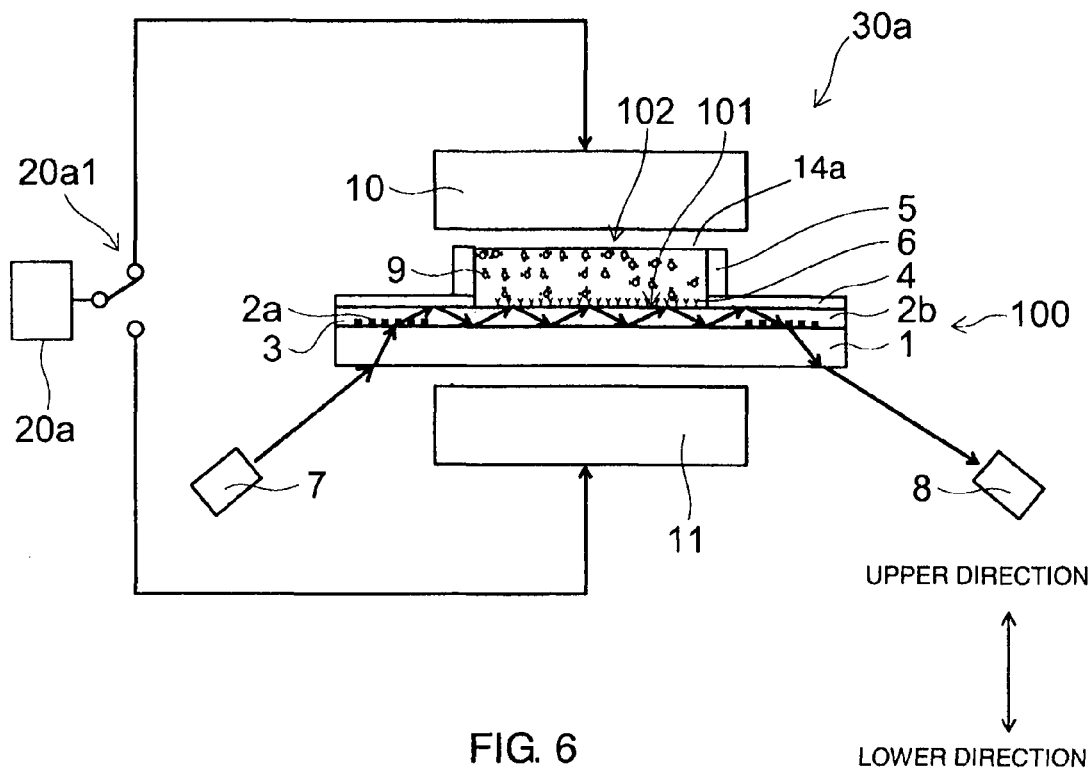
FIG. 6 is a schematic diagram illustrating a configuration of a measuring system which uses an optical waveguide according to a second embodiment.

FIG. 6 is a schematic diagram illustrating a configuration of a measuring system which uses an optical waveguide according to the second embodiment. A measuring system 30a according to the embodiment can further include the magnetic field applying unit 11 in addition to the configuration of the measuring system 30 of the first embodiment illustrated in FIG. 1.

The magnetic field applying unit 11 applies a magnetic field to the optical waveguide type sensor chip 100 in the direction toward the optical waveguide 3 when seen from the magnetic fine particle 9 by application of a magnetic field, the magnetic fine particles 9 can be moved in the direction toward the optical waveguide 3.

The magnetic field applying unit 11 is arranged at a position in a direction in which the optical waveguide 3 is present when seen from the magnetic fine particles 9, and is provided in a downward direction from the sensor chip 100.

The magnetic field applying unit 11 is a ferrite magnet or an electromagnet as in the magnetic field applying unit 10. It is desirable to adjust a current using the electromagnet in order to dynamically adjust the magnetic field intensity. However, using the ferrite magnet, the intensity of the magnetic field of the magnet itself or the relative position between the sensor chip 100 and the magnet can be changed so as to adjust an output magnetic field intensity. For example, when the ferrite magnet is disposed below the sensor chip 100 and a spacer is provided between the magnet and the sensor chip 100, the thickness of the spacer is changed so that the magnetic field intensity can be adjusted. When the electromagnet is used as the magnetic field applying unit 11, a coil is disposed in the direction toward the optical waveguide 3 when seen from the magnetic fine particles. A current is supplied to the coil and the current value is changed so that the magnetic field intensity can be adjusted.

The system 30a of the embodiment can further include a control unit 20a. The control unit 20a controls the intensity of the magnetic field applied to the magnetic field applying units 10, 11 or one of them. In this case, for example, as illustrated in FIG. 6, a common control unit 20a and a selection switch 20a1 can be provided for the magnetic field applying units 10, 11. A control unit for the magnetic field applying units 10, 11 can individually be provided. A control unit which controls the magnetic field intensity on the magnetic field applying units 10, 11 at the same time can be provided. The magnetic field intensity is controlled as needed so that the control unit 20a can be configured such that the dynamically appropriate magnetic field intensity is obtained.

The control unit 20a can control the timings at which the magnetic fields are applied from the magnetic field applying units 10, 11 respectively. By the control of the timings, the magnetic field applying units 10, 11 can alternately generate the magnetic fields according to a predetermined condition, for example, predetermined times, or time periods during which predetermined magnetic fields are continuously applied.

FIGS. 7A to 7C are diagrams illustrating steps of a method of measuring subject substances contained in a specimen solution using the above measuring system 30a. FIGS. 7A to 7C illustrate states of the reaction region 102 in respective steps. The steps of FIGS. 7A and 7C are the same as those of FIGS. 3A and 3C. In addition, the method using the measuring system 30a for measuring a difference between signal intensity ratios detected using the light receiving element 8 to measure a concentration of antigens contained in a specimen solution is also the same as the above method, and the processing of the optical detection signal obtained from the light receiving element 8 in the measuring system 30a is performed by the same processing unit (not illustrated) as the signal processing unit 8a of FIG. 1.

The step of FIG. 7B is different from the step of FIG. 3B. As indicated by an arrow of FIG. 7B, the magnetic field applying unit 11 applies a magnetic field in a settling direction, that is, a direction toward the optical waveguide 3 when seen from the magnetic fine particles 9, for example, a downward direction of FIG. 6. By the application of the magnetic field, the magnetic fine particles 9 are attracted toward the sensing area 101. At this time, the first substances 6, for example, primary antibodies fixed to the sensing area 101 and the second substances 13, for example, secondary antibodies fixed to the fine particles of the magnetic fine particles 9 are bonded to each other through the subject substances 14, for example, through antigens by an antigen-antibody reaction. By this reaction, the magnetic fine particles 9 are bonded to the sensing area 101.

In this case, the application of the magnetic field in the downward direction illustrated in FIG. 7B and the application of the magnetic field in the upward direction illustrated in FIG. 7C can be alternately repeated.

When the magnetic fine particles 9 is attracted toward the optical waveguide 3 by the application of the magnetic field in the downward direction illustrated in FIG. 7B, part of the subject substances 14 remain in the specimen solution in a state in which the part of the subject substances are not bonded to any one of the first substances 6 or the second substances 13, or are bonded to the second substances 13 fixed to the surfaces of the fine particles of the magnetic fine particles 9 but not bonded to the first substances 6 fixed to the sensing area 101. Further, the non-specifically absorbed magnetic fine particles 9 are present in the sensing area 101.

In the step of FIG. 7C, a magnetic field of an intensity, at which the magnetic fine particles 9 bonded to the first substances by an antigen-antibody reaction can not be separated, is applied, and the magnetic fine particles 9 which are not bonded to the first substances by an antigen-antibody reaction are moved in a direction different from that to the optical waveguide 3.

Subsequently, return to FIG. 7B, the magnetic field is applied in the direction toward the optical waveguide 3 so that the magnetic fine particles 9 which are not bonded by an antigen-antibody reaction are attracted in the direction toward the optical waveguide 3. By this operation, the subject substances 14 or the subject substances 14 bonded to the second substances 13 fixed to a surface of each fine particle 12 are newly bonded to the first substances 6 fixed to the sensing area 101.

By repeating this process, the number of the magnetic fine particles 9 which are not bonded to the sensing area 101 by an antigen-antibody reaction can be decreased, and the number of the magnetic fine particles 9 bonded to the sensing area 101 by an antigen-antibody reaction can be increased. As a result, the S/N ratio can be better.

According to the measurement of the embodiment, when the magnetic field is applied from the magnetic field applying unit 11 to the magnetic fine particles 9, the magnetic fine particles 9 can be attracted toward the sensing area 101. As a result, more magnetic fine particles 9 become easier to be bonded to the sensing area 101, thus the sensitivity in the detection of the subject substances 14 can be better.

Since the magnetic fine particles 9 and the specimen solution are introduced into the reaction region 102 and then the magnetic fine particles 9 are promptly attracted in the direction of the sensing area 101, it is possible to shorten a time necessary for the natural settling of the magnetic fine particles 9, which allows performing the measurement in a short time. It is possible to promote the bonding between the magnetic fine particles 9 and the sensing area 101 before the interaction and aggregation of the magnetic fine particles 9 advance. With such promoted bonding, it is possible to increase the coefficient of utilization of the subject substances 14 in the bonding between the magnetic fine particles 9 and the sensing area 101, the higher detection sensitivity is obtained.

In addition, since the magnetic fine particles 9 are moved by both or any one of the magnetic field applying units 10, 11, the specimen solution and the magnetic fine particles 9 can be mixed. With the mixing, the antigen-antibody reaction of the subject substances 14, for example, the antigens and the magnetic fine particles 9 contained in the specimen solution is promoted, and the measurement with the high detection sensitivity can be performed in the shorter time. The application of the magnetic field in the upward direction using the magnetic field applying unit 10And the application of the magnetic field in the downward direction using the magnetic field applying unit 11 are repeated, and the magnetic fine particles 9 are moved in a reciprocating manner, thereby further mixing the magnetic particles. By such a reciprocating movement, the number of chances in which the magnetic fine particles 9 are bonded to the sensing area 101 through the subject substances 14 increases, thus the subject substances 14 can be detected in the shorter time. In addition, the possibility that the magnetic fine particles 9 are bonded to the sensing area 101 can increase, and the detection sensitivity and the measurement precision of the subject substances 14 can be improved. For example, these are more effective when the subject substances 14 are present in a low concentration.

In the measurement according to the embodiment, since the magnetic fine particles 9 can be mixed using the magnetic field, a mixing operation by hand or a mixing mechanism with a pump is not needed, and a measuring system which is easily operated and is small in size can be realized. For example, when the application of the magnetic field using the control unit 20a is automatic, only an operation in which the specimen solution is introduced into the sensor chip 100 is to be carried out by a measurer, and subsequent processes and the measurement can automatically be performed.

Furthermore, In a case where fine particles having a superparamagnetic property in which the magnetism is promptly eliminated when application of magnetic field stops are used as the fine particles of the magnetic fine particles 9, even when the magnetic fine particles 9 are gathered due to the magnetism when magnetic field is applied to the magnetic fine particles, the magnetic fine particles can be dispersed again when the application of the magnetic field stops.

Even if the magnetic fine particles 9 are gathered when the magnetic field is applied to the magnetic fine particles, aggregations of the magnetic fine particles 9 can be dispersed again in a manner such that the application of the magnetic field stops before the aggregation of the magnetic fine particles 9 reaches the vicinity of the sensing area 101. Thus, the magnetic fine particles 9 can reach the sensing area 101 in a dispersed state. In this way, an increase in the measurement noise due to aggregation of the magnetic fine particles 9 can be prevented.

In order to further improve the re-dispersion property of the magnetic fine particles when the application of the magnetic field to the magnetic fine particles stops, the surfaces of the fine particles of the magnetic fine particles 9 can be made to have positive or negative charges. Alternatively, a dispersing agent such as a surface acting agent can be added onto the surfaces of the fine particles of the magnetic fine particles 9 as dispersing medium.

According to the embodiment, since the magnetic field intensity of the magnetic field applying units 10, 11 is appropriately controlled by the control unit 20a, the detection sensitivity and the measurement precision of the subject substances 14 can be improved.

In the first and second embodiments, a case is described in which the optical waveguide is disposed in a natural settling direction when seen from the magnetic fine particles. But, in a third embodiment to be described below, the optical waveguide is present in a direction opposite to the natural settling direction when seen from the magnetic fine particles.

FIG. 8 is a schematic diagram illustrating a configuration of a measuring system using an optical waveguide according to a third embodiment. A measuring system 30b according to the embodiment uses a container 15 which is a holding unit, instead of the frame 5 provided in the measuring system 30a of the second embodiment illustrated in FIG. 6. The cross-section of the container 15 is formed in a concave shape so as to hold a liquid without dropping the liquid from the container 15. The arrangement of the other main components is reversed up and down to those of the other main components illustrated in FIG. 6. Specifically, in the embodiment, a magnetic field applying unit 10 is disposed below an optical waveguide type sensor chip 100, and a magnetic field applying unit 11 is disposed above the optical waveguide type sensor chip 100. With such an arrangement, the magnetic field applying unit 10 applies the magnetic field from bottom, and the magnetic field applying unit 11 applies the magnetic field from above. In this case, the magnetic field applying unit 10 can not be essential.

The measuring system 30b illustrated in FIG. 8 includes the container 15 which has a concave cross-section, instead of the frame 5, in order to hold the mixture dispersion liquid of a specimen solution and magnetic fine particles 9. The container 15 and a sensing area 101 form a reaction region 102a which serves as a closed area except for a liquid introducing opening portion or an air hole (neither of which are illustrated).

The measuring system 30b of the embodiment can further include a control unit 20b. The control unit 20b controls the intensity of the magnetic field which is generated by the magnetic field applying units 10, 11, or any one of the magnetic field applying units. In this case, for example, as illustrated in FIG. 8, control units 20b1, 20b2 which are independent from the magnetic field applying units 10, 11 can be provided. Alternatively, a common control unit and a selection switch (not illustrated) can be provided for the magnetic field applying units 10, 11. In addition, a control unit which controls the magnetic field intensity on the magnetic field applying units 10, 11 at the same time can be provided. The control unit 20b controls the magnetic field intensity as needed so that the dynamically appropriate magnetic field intensity can be obtained.

The control unit 20b can control the timing of application of the magnetic field which is generated from the magnetic field applying units 10, 11. By the control of the timing, the magnetic field applying units 10, 11 can alternately generate magnetic field according to a predetermined condition, for example, predetermined times or time periods for which predetermined magnetic fields are continuously applied.

FIGS. 9A to 9C are diagrams illustrating steps of a method of measuring an amount of subject substances contained in a specimen solution using the measuring system 30b of FIG. 8. FIGS. 9A to 9C illustrate states of a reaction region 102a. The method of measuring a difference between signal intensity ratios detected using the light receiving element 8 to obtain the amount or a concentration of the subject substances, for example, a concentration of antigens contained in a specimen solution is the same as the method of using the measuring system 30 of the first embodiment, and the processing of a signal detected from the light receiving element 8 is performed by the same processing unit (not illustrated) as the signal processing unit 8a of FIG. 1.

The method using the measuring system 30b shown in FIG. 8 will be described in detail.

A measuring system 30b illustrated in FIG. 8 is prepared. Subsequently, as illustrated in FIG. 9A, a mixture dispersion liquid of a specimen solution and magnetic fine particles 9 is charged into the reaction region 102a which is formed by the container 15 and the sensing area 101 of FIG. 8. The method of charging the mixture dispersion liquid is the same as the method described in the measurement according to the first embodiment. It is desirable to use an inflow method of flowing through a liquid introducing opening portion (not illustrated), in order to introduce the specimen solution into the container 15. Contaminants 17 which are settled by its own weight can be contained in the specimen solution. As the contaminants 17, for example, a blood component in blood can be exemplified. When the contaminants 17 are present near the sensing area 101, the contaminants can serve as a scatter which causes noise in the measurement, or the magnetic fine particles 9 can be prevented from reaction of bonding to the sensing area 101, which can degrade the measurement precision.

Subsequently, as illustrated in FIG. 9B, magnetic field is applied from the magnetic field applying unit 11, in a direction toward the sensing area 101 as indicated by an arrow when seen from the magnetic fine particle 9. By the application of the magnetic field, the magnetic fine particles 9 are attracted toward the sensing area 101. At this time, first substances 6, for example, primary antibodies fixed to the sensing area 101, and second substances 13, for example, secondary antibodies fixed to surfaces of the fine particles 12 are bonded to each other through subject substances 14 to be measured, for example, antigens by an antigen-antibody reaction. Accordingly, the magnetic fine particles 9 are bonded to the sensing area 101. At the same time as the bonding, the contaminant 17 which have a property of settling move in a downward direction, i.e., a direction opposite to the sensing area 101 of FIG. 9B by their own weights.

Furthermore, as illustrated in FIG. 9C, a magnetic field is applied from the magnetic field applying unit 10 in the downward direction indicated by an arrow. 13y the application of the magnetic field, the magnetic fine particles 9 which are absorbed to the sensing area 101 move in a settling direction, without using the subject substances 14 and an antigen-antibody reaction, and are eliminated from the sensing area 101. An application of magnetic field in the upward direction indicated by the arrow of FIG. 9B can be stopped simply by using a measuring system without employing the magnetic field applying unit 10. By the application, magnetic fine particles 9 which are absorbed to the sensing area 101 can be moved in the downward direction by their own weight, without using subject substances 14 and an antigen-antibody reaction. However, according to this method, when a absorption force of the magnetic fine particles 9 with respect to the sensing area 101 is larger than a force in the downward direction corresponding to their own weights, it is difficult to eliminate the magnetic fine particles 9 which are absorbed to the sensing area 101. Even in the step illustrated in FIG. 9C, the contaminants 17 having the property of settling keep moving in the downward direction i.e. the direction opposite to the optical waveguide 3 of FIG. 9C by their own weights.

In the measurement using the measuring system of the embodiment, the application of the magnetic field in the upward direction illustrated in FIG. 9B, the application of the magnetic field in the downward direction illustrated in FIG. 9C, or the settling of the magnetic fine particles 9 by their own weights can alternately be repeated, thereby mixing the specimen solution, the magnetic fine particles 9, the subject substances 14, and the contaminants 17.

According to the embodiment, as illustrated in FIG. 8, the sensing area 101 is located at an upper position seen from the magnetic fine particles 9, and the magnetic field in the downward direction is applied from the magnetic field applying unit 11 to the magnetic fine particle 9. By the application of the magnetic field, the magnetic fine particles 9 can be attracted toward the sensing area 101, and, simultaneously, the contaminants 17 can be settled in the downward direction. By this settling, the contaminants 17 can be naturally moved to the outside of the region where the evanescent light is present in the vicinity of the sensing area 101. As a result, the measurement precision can further be improved without eliminating the contaminants 17 by filtering or the like in advance.

Figure 10A:
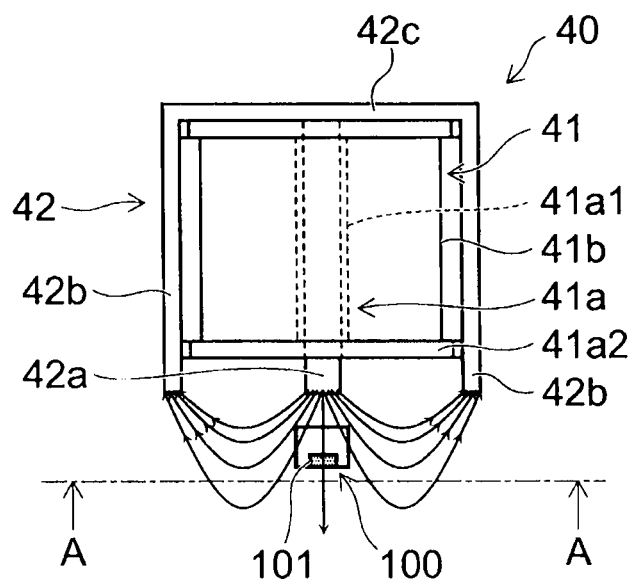
FIG. 10A is a schematic diagram illustrating an example of a magnetic field applying unit.
Figure 10B:
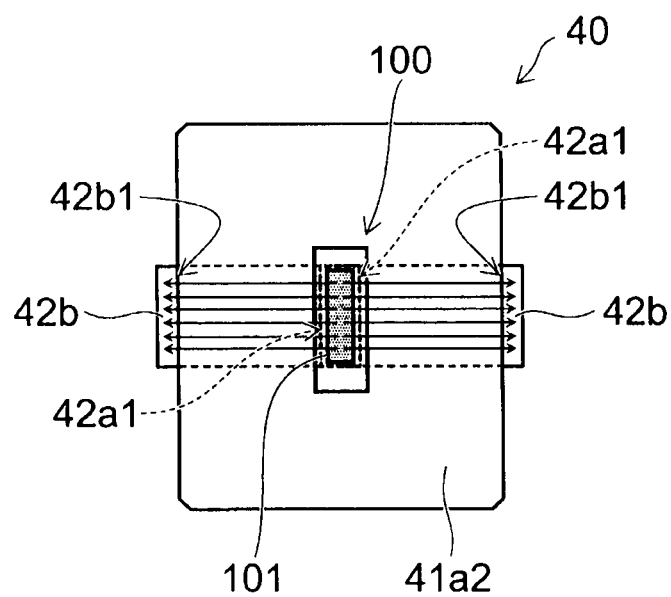
FIG. 10B is a diagram illustrating the magnetic field applying unit of FIG. 10A when seen in a direction indicated by an arrow A.
Figure 10C:
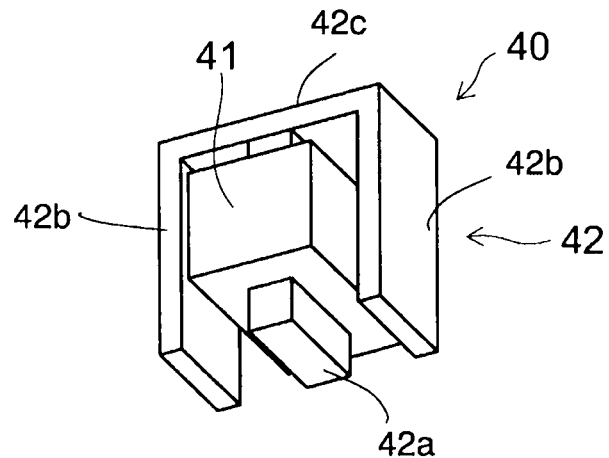
FIG. 10C is a schematic perspective view illustrating the magnetic field applying unit of FIG. 10A.

Hereinafter, a specific structure of a magnetic field applying unit will be described. FIGS. 10A to 10C are diagrams illustrating an example of a magnetic field applying unit. FIG. 10A is a schematic diagram illustrating an example of a magnetic field applying unit. FIG. 10B is a diagram illustrating the magnetic field applying unit of FIG. 10A when seen from the direction of an arrow taken along a line A-A. FIG. 10C is a schematic perspective view illustrating the magnetic field applying unit of FIG. 10A.

The structure of a magnetic field applying unit 40 illustrated in FIGS. 10A to 10C can be applied to any one of the magnetic field applying unit 10And the magnetic field applying unit 11. As illustrated in FIGS. 10A to 10C, the magnetic field applying unit 40 includes a coil 41 and a magnetic core 42. As described in detail below, the core 42 includes a first plate-like core portion 42a, a pair of second plate-like core portions 42b, and a connection portion 42c. The coil 41 is provided inside the core 42, and includes an insulating wire 41b and a bobbin 41a which holds the insulating wire 41b. The bobbin 41a includes a cylindrical portion 41a1 around which the insulating wire 41b is wound, and includes flanges 41a2 which are provided at both ends of the cylindrical portion 41a1. The first core portion 42a penetrates into the cylindrical portion 41a1 in a vertical direction of FIG. 10A.

Since the bobbin 41a is formed in a simple cylindrical shape, when the insulating wire 41b is to be wound on the bobbin 41a, the wire can be rapidly wound. Accordingly, it is possible to shorten the time of the wire winding step. In addition, since the magnetic field applying unit 40 can be manufactured by a simple assembly in which the bobbin 41a having the insulating wire 41b wound on the bobbin is inserted into the core 42, it is possible to shorten the time of the assembly step. In this case, the bobbin 41a is not essential, and can be appropriately provided if necessary. For example, the coil 41 can be formed in a manner such that the insulating wire 41b is wound on the core.

The second core portions 42b are provided outside the coil 41 and to be symmetrical to each other with the first core portion 42a interposed between the portions 42b. The connection portion 42c mechanically or magnetically connects each one of the end portions of the first core portion 42a to each one of the end portions of the second core portions 42b.

The first core portion 42a, the second core portions 42b, and the connection portion 42c can be separated from each other. In this case, it is possible to improve the assembly workability when the coil 41 is assembled to the core 42. As illustrated in FIG. 10B, edges 42b1 of the second core portions 42b facing the first core portion 42a or edges 42a1 of the first core portion 42a facing the second core portions 42b are set to be parallel to the direction in which the light is propagated inside the optical waveguide 3.

According to this configuration, since the uniform magnetic field can be applied to the sensing area 101, the distribution of the magnetic fine particles 9 in the sensing area 101 can be uniformly set. In addition, in the direction in which the light is propagated inside the optical waveguide 3, the length of an end surface of each of the first core portion 42a and the second core portions 42b on a side of the sensing area 101 which extends in a vertical direction of the drawing is set to be equal to or longer than the length of the sensing area 101 in the vertical direction of the drawing. According to this setting, since the magnetic field can be applied to the entire sensing area 101, the magnetic fine particles 9 can be moved in the entire sensing area 101.

The end surface of the first core portion 42a on the side of the sensing area 101 and the end surfaces of the second core portions 42b on the side of the sensing area 101 side are flat. The end surfaces are flat so that the distance between the first core portion 42a and the sensing area 101 and the distances between the second core portions 42b and the sensing area 101 can be shortened. Furthermore, the first core portion 42a and the second core portions 42b may be formed in a manner such that cross-sectional areas of parts of the core portions 42a, 42b become smaller as the parts of the portion 42a, 42b are closer to the sensing area 101.

The first core portion 42a and the second core portions 42b can be formed in a shape in which front end portions on the side of the sensing area 101 is thinned. Magnetic fluxes can be concentrated by using such a shape. Thus, a strong magnetic field can be applied. The end portions of the second core portions 42b can be formed in a shape in which the end portions are inclined in a direction in which the end portions move closer to each other. The magnetic field can easily be generated by using such a shape.

The core 42 can be formed of a material having residual magnetization smaller than that of carbon steel, for example, pure iron. When the core 42 is formed of such a material, it is possible to suppress the influence of the residual magnetic field of the core 42 with respect to the movement of the above magnetic fine particles 9 when the application of the magnetic field is stopped by the control unit 20. The first to third core portions of the core 42 may have a structure in which thin magnetic plates such as silicon steel plates coated with insulator are stacked in a direction parallel to the magnetic field. Such a thin plate composing each core portion can be easily and rapidly processed by pressing. Furthermore, when the pressing and the stacking are simultaneously performed, a part of the core 42 may protrude in the thickness direction so as to join and fix the stacked plates composing the core easily. It is possible to reduce the number of processing steps by using such a structure.

The core 42 has anisotropy in a direction in which the magnetic fluxes flow. The magnetic fluxes inside the core 42 flow in a planar direction easily, but are difficult to flow in a thickness direction. Accordingly, when the stacking direction is set to be parallel to the direction in which the light is propagated inside the optical waveguide 3, the leakage of the magnetic fluxes to outside of the sensing area 101 is reduced so that a desired magnetic field can be generated with a smaller electromagnetic force. As a result, the operating efficiency of the measuring system can be improved.

The core 42 can have a structure in which magnetic powders such as ferromagnetic fine powders such as carbonyl iron powders coated with insulator are pressed and molded. Eddy current loss can be reduced with such a structure of the core 42. In FIGS. 10A to 10C, the coil 41 is supported by the first core portion 42a, but the example is not limited to the configuration. For example, the second core portions 42b may be provided with coils, or both of the first core portion 42a and the second core portions 42b may be provided with coils. The connection portion 42c may be provided with the coils.

In addition, the coils may be separately provided in the left and right second core portions 42b. In this case, supply of current can be independently controlled. For example, a current may be controlled to flow only in the right coil. The current may be controlled to flow only in the left coil. The current may be controlled to flow in both of the left and right coils simultaneously. In such a control, the movement of the magnetic fine particles 9 in the vertical and horizontal directions can be controlled. Accordingly, since the number of chances in which the magnetic fine particles 9 and the subject substances 14 come into contact with each other can be increased, the detecting precision can be improved.

Figure 11A:
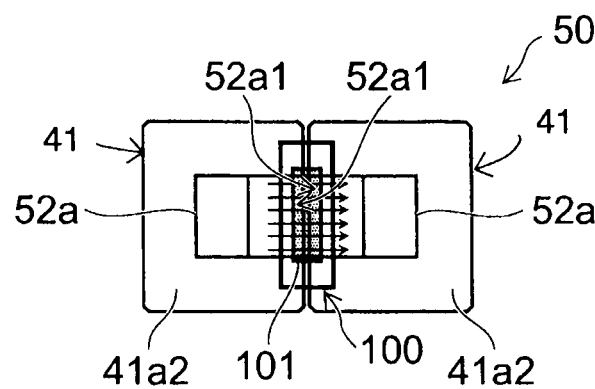
FIG. 11A is a schematic diagram illustrating another example of the magnetic field applying unit.
Figure 11B:
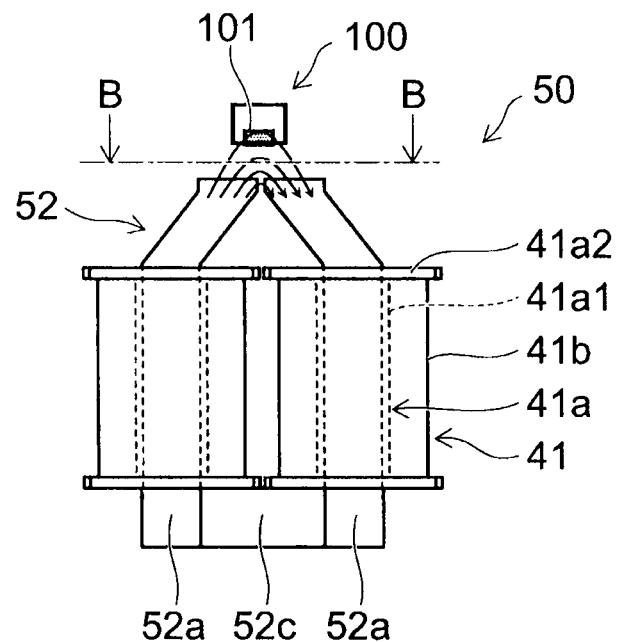
FIG. 11B is a diagram illustrating the magnetic field applying unit of FIG. 11A when seen upward from the bottom in the drawing paper.
Figure 11C:
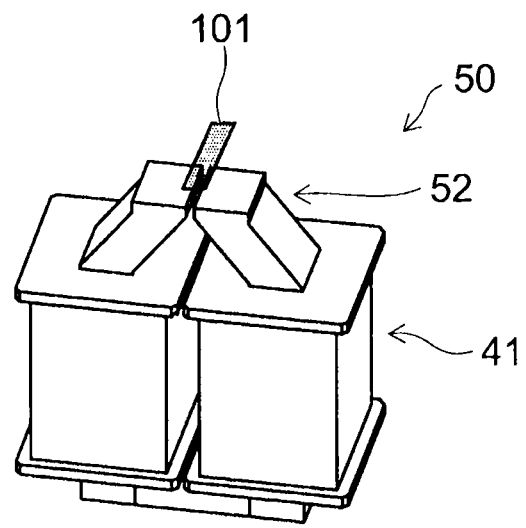
FIG. 11C is a schematic perspective view illustrating the magnetic field applying unit of FIG. 11A.

Another example of the magnetic field applying unit will be described. FIGS. 11A to 11C are schematic diagrams illustrating a configuration of an example of the magnetic field applying unit. FIG. 11A shows a schematic diagram the example. FIG. 11B is a diagram illustrating the example shown in FIG. 11A when seen upward from bottom in FIG. 11A. FIG. 11A is a diagram illustrating the example illustrated in FIG. 11B when seen in a direction indicated by an arrow B.

FIG. 11C is a schematic perspective view illustrating the example illustrated in FIG. 11A. A magnetic field applying unit 50 which is illustrated in FIGS. 11A to 11C can be used as any one of the above first magnetic field applying units 10, 11.

As illustrated in FIGS. 11A to 11C, the magnetic field applying unit 50 includes coils 41 and a core 52. The coils 41 are the same as the coils illustrated in FIGS. 10A to 10C. The core 52 includes two core portions 52a which are provided with the coil 41 and a connection portion 52c which mechanically and magnetically connects one end portions of the core portions 52a to each other. In this case, the core portions 52a may be separated from the connection portion 52c. When the core portions are separated in this way, the assembly workability which is obtained when the coils 41 are assembled to the core 52 can be improved.

Furthermore, as illustrated in FIGS. 11A and 11B, edges 52a1 of the core portions 52a facing the sensing area 101 are parallel to the direction in which light is propagated inside the optical waveguide 3. With such an arrangement, a uniform magnetic field can be applied, and, thus, the distribution of the magnetic fine particles 9 in the sensing area 101 can be uniformly set. In the direction in which the light is propagated inside the optical waveguide 3, the length of each end surface of the core portions 52a facing the sensing area 101 in the vertical direction of the drawing is equal to or longer than the length of the sensing area 101 in the vertical direction of the drawing. With such setting, a magnetic field can be applied to the entire sensing area 101, and, thus, it is possible to move the magnetic fine particles 9 in the entire sensing area 101.

End surfaces of the core portions 52a on a side of the sensing area 101 are flat. Since the end surfaces on the side of the sensing area 101 are formed as a plane, the distance between the core portions 52a and the sensing area 101 can be reduced. The core portions 52a can be formed in a shape in which parts of the cross-sectional areas of core portions 52a become smaller as the parts are closer to the sensing area 101. In other words, the core portions 52a can be formed in a shape in which front ends of the core portions on the side of the sensing area 101 are thinned. With such a shape, magnetic fluxes generated can be concentrated, and, thus, a strong magnetic field can be applied. The end portions of the core portions 52a on the side of the sensing area 101 can be formed in a shape in which the end portions are inclined so as to be close to each other. The magnetic field can easily be generated by using such a shape.

A non-magnetic material, for example, a spacer of a resin or copper may be provided between the end portions of the core portions 52a on the side of the sensing area 101. When such a spacer is provided, the dimension of the gap can easily be controlled. In this case, when the magnetic field is applied to the core 52, the magnetic absorbing force is exerted in a direction in which the gap decreases, but the dimension of the gap can be maintained by providing the spacer. Accordingly, it is possible to suppress change in distribution of the magnetic fluxes inside the sensing area.

The core 52 can be formed of the same material as that of the above core 42. For example, the core 52 can be formed of a material having residual magnetization smaller than that of carbon steel, for example, pure iron. When the core 52 is formed of such a material, it is possible to suppress an influence of the residual magnetic field of the core 52 with respect to the movement of the above magnetic fine particles 9 when the application of the magnetic field is stopped by the control unit 20. In FIGS. 11A and 11B, two core portions 52a are provided with the coils 41 respectively, but the example is not limited to the configuration. For example, only one of the two core portions 52a may be provided with the coil 41, and the connection portion 52c may be provided with the coil 41.

When two core portions 52a are provided with the coils 41, it is possible to suppress the height of the magnetic field applying unit 50 to become low. When only one of the core portions 52c is provided with one coil 41, the number of the coils 41 can be small. Accordingly, it is possible to decrease the number of wire winding and assembly steps, in addition to the decreased number of components.

Figure 12A:
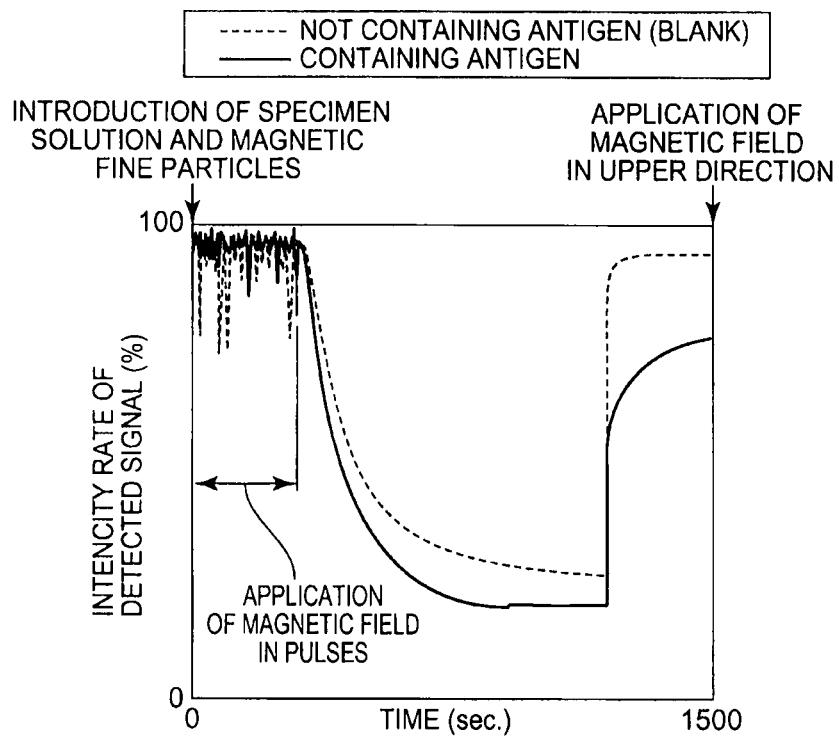
FIGS. 12A and 12B are graphs illustrating operations and effects of the magnetic field applying unit.
Figure 12B:
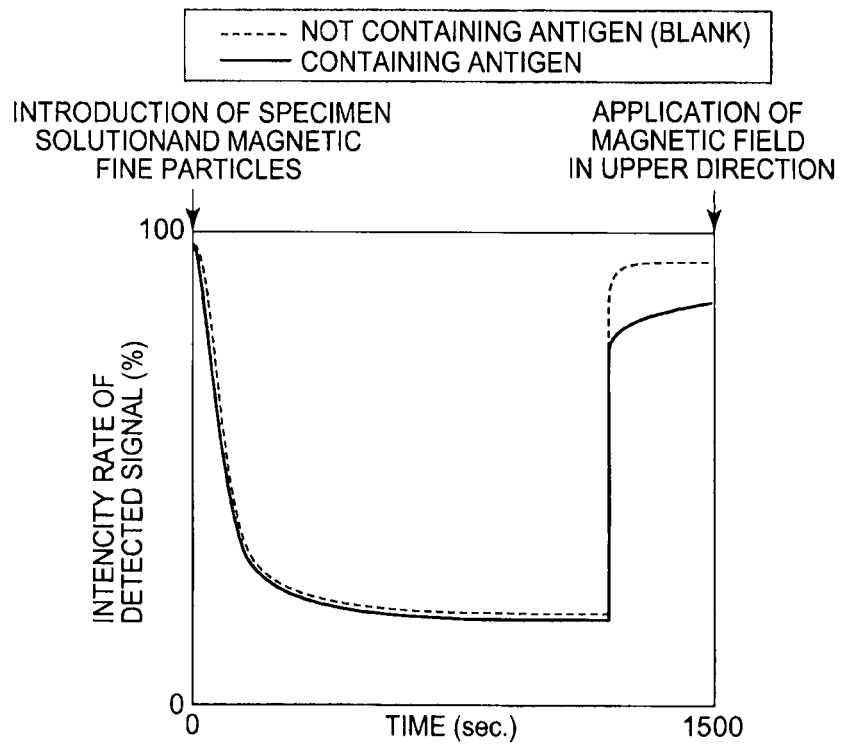

Hereinafter, an operation and effects of the above magnetic field applying units will be further described. FIGS. 12A and 12B are graphs illustrating an example operation and effects of the magnetic field applying unit 10 used in the measuring system 30 illustrated in FIG. 1, respectively. In this case, application of magnetic field can be controlled by the control unit 20. FIG. 12A illustrates a case including a step of eliminating the magnetic fine particles 9 which may cause noise in measurement by the magnetic field applying unit 10 using the measuring system 30. FIG. 12B illustrates a case including a step of mixing a dispersion liquid of the magnetic fine particles 9 and a specimen solution by the magnetic field applying unit 10.

As illustrated in FIG. 12A, when the dispersion liquid of the magnetic fine particles 9 and the specimen solution are mixed and the obtained mixture liquid is introduced into the sensing area 101 illustrated in FIG. 1, an intensity ratio of optical detection signals decreases with increase in the density of the magnetic fine particles near the sensing area 101 according to settling of the magnetic fine particles 9. Subsequently, when a magnetic field in the upward direction is applied by the magnetic field applying unit 10, the magnetic fine particles 9, which are absorbed to the sensing area 101 and can cause noise in the measurement, are eliminated. Accordingly, the intensity ratio of the optical detection signals increases again, and is saturated at a value which is lower than an intensity ratio of the optical detection signals.

Further, as illustrated in FIG. 12B, the dispersion liquid of the magnetic fine particles 9 and the specimen solution are mixed, the obtained mixture liquid is introduced into the sensing area 101, and a magnetic field going in an upward direction is applied in pulses by the magnetic field applying unit 10. For example, the magnetic field progressing in the upward direction is applied every ten second by the magnetic field applying unit 10. Subsequently, when the magnetic fine particles 9 are settled, the intensity ratio of optical detection signals decreases with increase of a density of the magnetic fine particles near the sensing area 101.

In addition, when the magnetic field going in the upward direction is applied by the magnetic field applying unit 10, the magnetic fine particles 9 which are absorbed to the sensing area 101 and may cause noise in the measurement are eliminated. Accordingly, the intensity ratio of the detection signals increases again, and is saturated at a value which is lower than the initial intensity ratio of the optical detection signals. In the case illustrated in FIG. 12B, the intensity ratio of the optical detection signals after the magnetic fine particles 9 which may cause noise in the measurement are eliminated is lower compared with the case of FIG. 12A. In the case of FIG. 12B, the amount of the magnetic fine particles 9 which are bonded to the sensing area 101 through the subject substances 14 is greater.

When the magnetic field going in the upward direction is applied in pulses by the magnetic field applying unit 10, the magnetic fine particles 9 and the specimen solution can be mixed. It is found that the reaction rate between the second substances 13 fixed to the fine particles composing the magnetic fine particles 9 and the subject substances 14 increases and that the amount of the magnetic fine particles 9 bonded to the sensing area 101 through the subject substances 14 increases. When the reaction rate between the second substances 13 fixed to the fine particles composing the magnetic fine particles 9 and the subject substances 14 can be increased, the sensitivity in detection of the subject substances 14 can be improved with higher precision.

In the above example, a case in which a magnetic field going in an upward direction is applied is described, but the example is not limited to the case. The magnetic field may be applied so that the magnetic fine particles 9 are moved to be separated from the sensing area 101. For example, in the case of the measuring system 30b illustrated in FIG. 8, the magnetic field progressing in the downward direction may be applied in pulses. The timing at which magnetic fields going in the upward direction and in the downward direction are applied may be shifted, and the magnetic field in the upward direction and the magnetic field in the downward direction can be applied in pulses. With such an application, the magnetic fine particles 9 and the specimen solution can be further mixed by the magnetic fields in the upward direction and the downward direction.

Figure 13A:
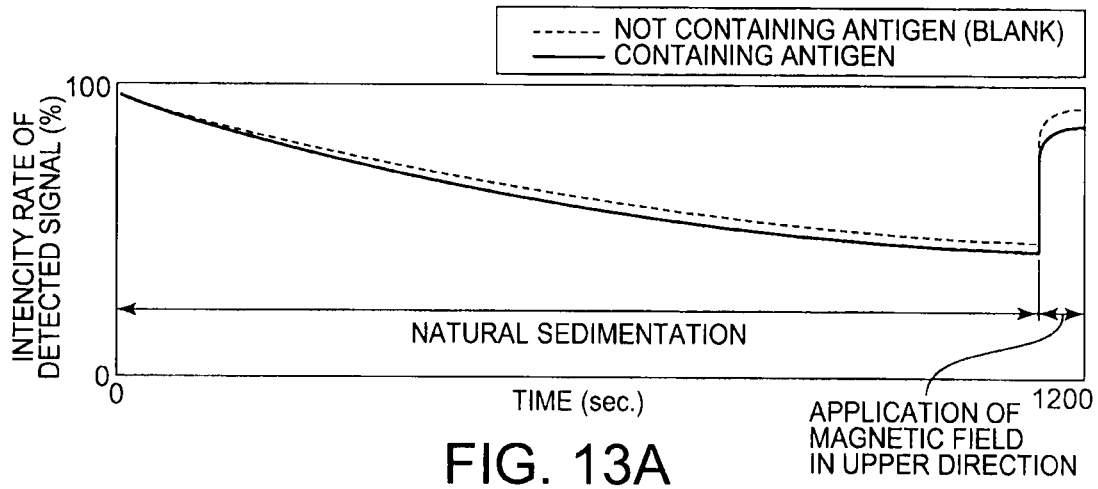
FIGS. 13A to 13C are graphs illustrating operations and effects of the magnetic field applying unit.
Figure 13B:
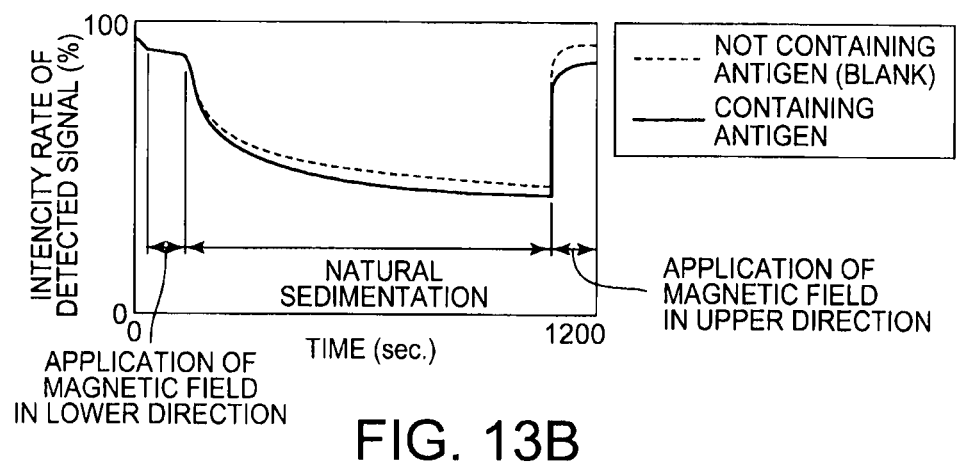
Figure 13C:
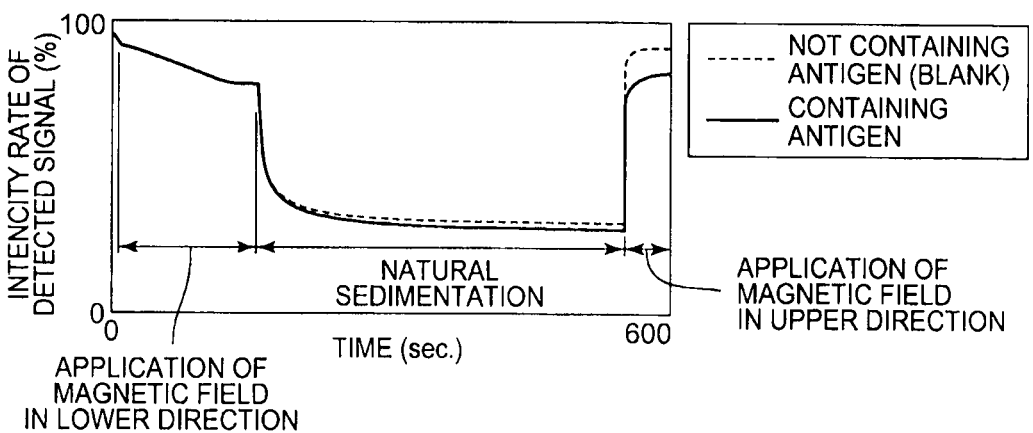

FIGS. 13A to 13C are respectively graphs illustrating an operation and effects of the magnetic field applying units 10, 11 provided in the measuring system 30a illustrated in FIG. 6. In this case, application of magnetic field can be controlled by the control units 20a, 20b. FIG. 13A illustrates a case where a magnetic field going in an upward direction is applied only by the magnetic field applying unit 10, and FIGS. 13B, 13C illustrate a case where a combination of application of a magnetic field going in a downward direction by the magnetic field applying unit 11 and application of magnetic field going in the upward direction by the magnetic field applying unit 10. In the case of the measurement illustrated in FIG. 13A, after a dispersion liquid of the magnetic fine particles 9 and a specimen solution are mixed and introduced into a reaction region 102, the magnetic fine particles 9 are naturally settled. In addition, after the intensity ratio of optical detection signals decreases to a predetermined value, the magnetic field going in the upward direction is applied so as to eliminate the magnetic fine particles 9 which are absorbed to the sensing area 101 and may cause noise in the measurement.

In the case of the measurement illustrated in FIGS. 13B and 13C, after the dispersion liquid of the magnetic fine particles 9 and the specimen solution are mixed and introduced into the reaction region 102, the magnetic field going in the downward direction is applied, so that the magnetic fine particles 9 move toward the sensing area 101. Subsequently, the application of the magnetic field going in the downward direction is stopped so that the magnetic fine particles 9 are naturally settled. In addition, after the intensity ratio of the optical detection signals decreases to a predetermined value, the magnetic field going in the upward direction is applied so that the magnetic fine particles 9 which are absorbed to the sensing area 101 and may cause noise in the measurement are eliminated.

Figure 14A:
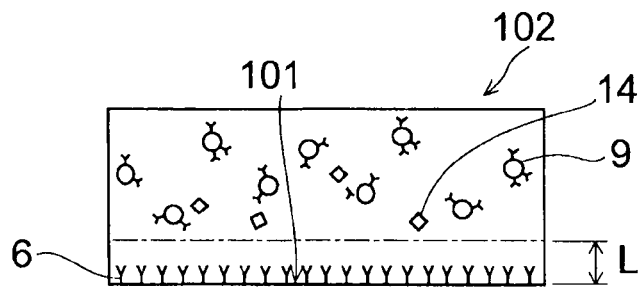
Figure 14C:
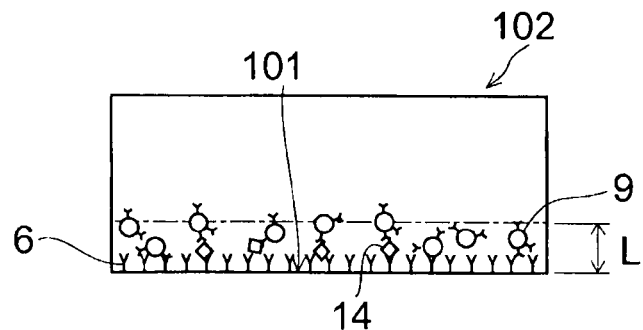
Figure 14D:
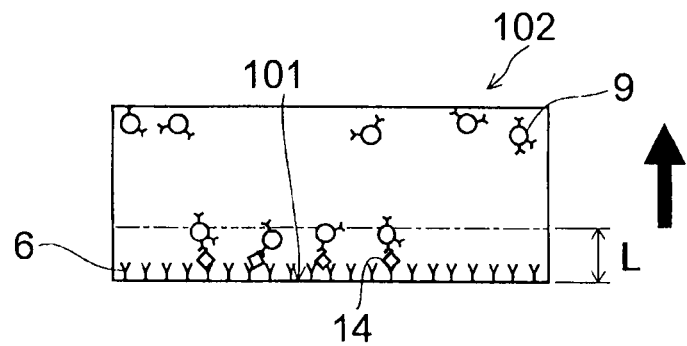

As illustrated in FIGS. 13A to 13C, when the magnetic field going in the downward direction is applied so as to move the magnetic fine particles 9 toward the sensing area 101, it is possible to shorten the time necessary until the magnetic field going in the upward direction can be applied, and, accordingly, the measurement time can be shortened. FIGS. 14A to 14D are diagrams illustrating steps of another method of measuring a concentration of the subject substances 14 using the measuring system 30a shown in FIG. 6. FIGS. 14A to 14D illustrate a state which occurs in a reaction region 102 respectively. The step of FIG. 14A is the same as that of FIG. 7A, the step of FIG. 14C is the same as that of FIG. 7B, and the step of FIG. 14D is the same as that of FIG. 7C. FIG. 14B1 illustrates a step in which a magnetic field going in the downward direction is not applied by the magnetic field applying unit 11.

In this case, the magnetic fine particles 9 contained in the specimen solution are settled (naturally settled) toward the sensing area 101 by the gravity. FIG. 14B2 illustrates a step in which a magnetic field is applied in a settling direction (a direction toward the optical waveguide 3, for example, the downward direction of FIG. 14) when seen from the magnetic fine particles 9 as depicted by an arrow by the magnetic field applying unit 11. In this case, the magnetic fine particles 9 are attracted toward the sensing area 101 by the natural settling caused by the gravity and the suction caused by application of the magnetic field going in the downward direction. However, as illustrated in FIG. 14B2, in this state, since most of the magnetic fine particles 9 stop along the magnetic force lines, a bonding reaction of the magnetic fine particles 9 with the first substances 6 does not occur. Accordingly, as illustrated in FIG. 14C, it is necessary to cause the bonding reaction to progress by natural dispersion after the external magnetic field is once set to zero. In FIGS. 14B1 and 14B2, a part of the magnetic fine particles 9 settled toward the sensing area 101 are bonded to the sensing area 101.

When a measuring system 30b illustrated in FIG. 8 is used as the measuring system employing the optical waveguide, for example, the magnetic field going in the downward direction is applied by the magnetic field applying unit 10. Then, it becomes possible to eliminate the magnetic fine particles 9 which are absorbed to the sensing area 101 and may cause noise in the measurement in a short time, compared with a case where magnetic fine particles are naturally settled. Thus, the measurement time can be shortened.

Hereinafter, a measuring system and a measuring method using an optical waveguide, an optical waveguide type sensor chip, and magnetic fine particles according to a fourth embodiment will be described. The measuring system of the embodiment has the same configuration as that of the measuring system illustrated in FIG. 1, except for the configuration of the magnetic fine particles. In the embodiment, a magnetic fine particle 9a illustrated in FIG. 15 or a magnetic fine particle 9b illustrated in FIG. 16 are used for the magnetic fine particles 9.

Figure 15:
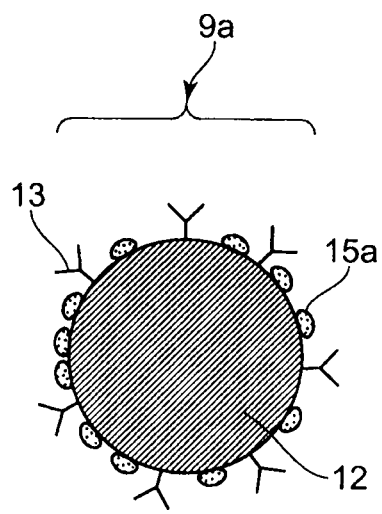
FIG. 15 is a schematic diagram illustrating another example of the magnetic fine particles.
Figure 16:
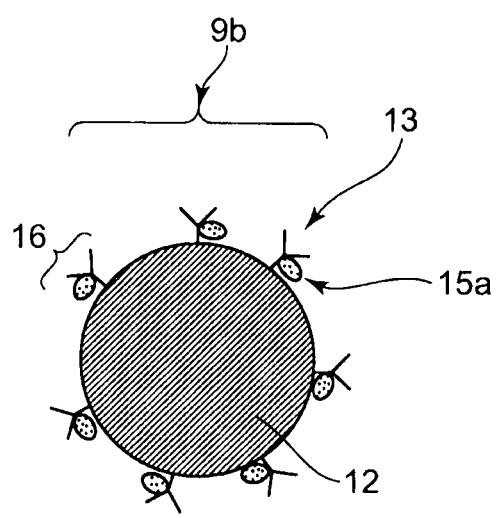
FIG. 16 is a diagram illustrating still another example of the magnetic fine particles.

In the magnetic fine particle 9a of FIG. 15, second substances 13 which specifically react with subject substances to be measured and marking bodies 15a which cause a color forming reaction are fixed to a surface of a fine particle 12 having a magnetic property. When the subject substances contained in a specimen solution 14a are antigens, antibodies (primary antibodies) can be used for the first substances 6 which are fixed to the sensing area 101 of the optical waveguide 3 constituting the optical waveguide type sensor chip 100. When the subject substances contained in the specimen solution 14a are antigens, antibodies (secondary antibodies) can be used for the second substances 13. The first substances 6 can be fixed to the surface the optical waveguide 3, for example, by hydrophobic interaction, chemical bonding, ionic bonding, coordinate bonding such as complex, or specific bonding using biological molecules (biotin-avidin bonding or bonding using histidine).

The marking bodies 15a are pigments which form color by an enzyme reaction, for example. As the pigments, 3, 3', 5, 5'-tetramethylbenzidine (hereinafter, simply referred to as 'TMBZ') may be used. Alternatively, the marking bodies 15a may be an enzyme which catalyzes the color forming reaction. Peroxidase may be used, as the enzyme. Plural marking bodies 15a can be fixed to the fine particles 12.

When the marking bodies 15a are fixed to the fine particles 12, light is absorbed by a color forming reaction, in addition to absorbing and scattering of the light by the fine particle. Accordingly, it is possible to improve the sensitivity in detection of the subject substances better, compared with a measuring method using a fine particle only or a measuring method using a color forming reaction only.

In the magnetic fine particle 9b of FIG. 16, second substances 13 bonded to marking bodies 15a, respectively i.e. second substances 13 with a marking are fixed to a surface of the fine particle 12. "16" shows a marking antibody when the second substances 13 with a marking are antibodies, for example.

The combination of the subject substances and the first substances or the second substances which have a property of specifically bonding to the subject substances is not limited to the combination of antigens and antibodies. For example, the combination of sugar and lectin, the combination of a nucleotide chain and a complementary nucleotide chain, the combination of ligand and a receptor can be used.

Magnetic fine particles 9 having a structure of the magnetic fine particle 9a or 9b, to which the second substances 13 and the marking bodies 15a are fixed, are dispersed and held in the sensing area 101 of the surface of the optical waveguide 3 to which the first substances 6 are fixed. The magnetic fine particles 9 can be dispersed and held, for example, in such a manner that slurry or a pad containing magnetic fine particles 9 and a water-soluble substance is applied to the surface of the optical waveguide 3 or to a surface of a member (not illustrated) facing the surface and is dried. Alternatively, the magnetic fine particles 9 can be dispersed in a liquid, and the liquid can be held in a region other than the reaction region 102 on the optical waveguide 3 or in a container.

The first magnetic field applying unit 10Applies a magnetic field to the optical waveguide type sensor chip 100. When the magnetic field is applied, the magnetic fine particles 9 can be moved along the magnetic field. The first magnetic field applying unit 10Are disposed in the direction opposite to the optical waveguide 3 when seen from the magnetic fine particles 9.

When the magnetic field is applied from the first magnetic field applying unit 10 to the magnetic fine particles 9, the magnetic fine particles 9 which are absorbed to the optical waveguide 3 can be separated from the optical waveguide 3 without using an antigen-antibody reaction. Accordingly, it is possible to measure the absorbency caused only by the magnetic fine particles 9 which are bonded to the surface of the optical waveguide through the antigens by an antigen-antibody reaction and to reduce the measurement error.

Furthermore, in the embodiment, the naturally settled magnetic fine particles 9 can be returned in an upward direction by the first magnetic field applying unit 10. By repeating the process in which the magnetic fine particles 9 are naturally settled and are returned in the upward direction by the first magnetic field applying unit 10, the subject measurement specimen solution and the magnetic fine particles 9 can be mixed. The mixing promotes bonding between the magnetic fine particles 9 and the first substances (the primary antibodies) fixed to the surface of the optical waveguide 3 through the subject substances (the antigens) which are contained in the specimen solution, by an antigen-antibody reaction. Accordingly, higher detection sensitivity can be obtained in a shorter time. Furthermore, the marking bodies 15a and the reagents 16 to be described below can be further mixed, and the color forming reaction can be further promoted. Particularly when the subject substances are at a low concentration, the detection sensitivity can be improved by such an effect.

The method of measuring subject substances using the above measuring system will be described by referring to FIGS. 17A to 17D.

Figure 17A:
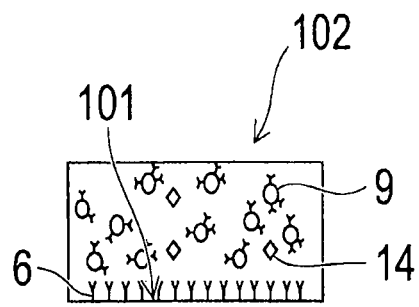
FIGS. 17A to 17D are diagrams illustrating another method of measuring subject substances to be measured contained in a specimen solution.

The measuring system illustrated in FIG. 1 is prepared. Subsequently, as illustrated in FIG. 17A, a specimen solution 14a is introduced into the optical waveguide 3 where the magnetic fine particles 9 having a structure of the magnetic fine particle 9a or 9b are dispersed and held, and the magnetic fine particles 9 are dispersed again. When the magnetic fine particles 9 are held in a region other than the reaction region 102 of the optical waveguide 3 or another container, a mixture dispersion liquid of a specimen solution and the magnetic fine particles 9 is introduced into the reaction region 102. Alternatively, after dispersion liquid of the magnetic fine particles 9 is introduced into the reaction region 102, a specimen solution may be introduced into the reaction region 102 so as to mix the solution and the liquid. The dispersion liquid of the magnetic fine particles 9 and the specimen solution can then separately be introduced. Such an introduction method can be performed by, for example, dripping or inflowing.

Figure 17B:
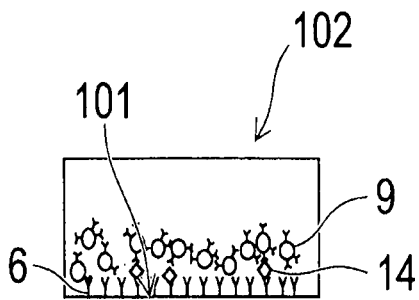

As illustrated in FIG. 17B, the magnetic fine particles 9 are settled onto the surface of the optical waveguide 3 by their own weights. At this time, first substances 6 (primary antibodies) fixed to the surface of the optical waveguide 3 and second substances 13 (secondary antibodies) fixed to the magnetic fine particles 9 are bonded through the subject substances 14 (the antigens) by an antigen-antibody reaction. Such bonding allows the magnetic fine particles 9 to be fixed to the surface of the optical waveguide 3.

Figure 17C:
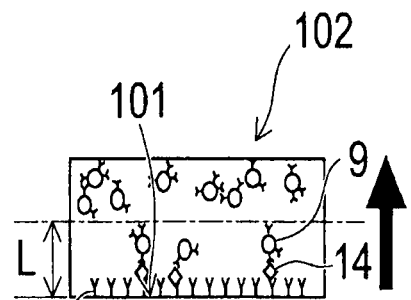

Subsequently, as depicted by an arrow of FIG. 17C, a magnetic field is applied in a direction (an upward direction) different from the settling direction when seen from the magnetic fine particles 9. As a result, the magnetic fine particles 9, which are absorbed to the surface of the optical waveguide 3 without using the subject substances 14 and without an antigen-antibody reaction, are moved in the direction (the upward direction) different from the settling direction and are eliminated from the surface of the optical waveguide 3.

Figure 17D:
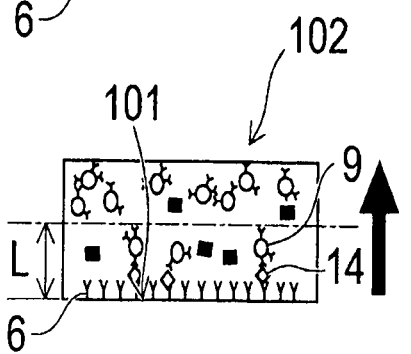

Furthermore, as illustrated in FIG. 17D, the reagents 16 which react with the marking bodies 15 to cause a color forming reaction are introduced into the reaction region 102. Such an introduction method can be performed by, for example, dripping or inflowing. In this case, in order to prevent the magnetic fine particles 9 from being naturally settled, it is desirable that the reagents 16 are introduced while the magnetic field is applied in the direction (the upward direction) different from the settling direction when seen from the magnetic fine particles 9. For example, when the marking bodies 15a are TMBZ as pigments, a mixture solution of peroxidase and hydrogen peroxide which is capable of forming color through a reaction with TMBZ can be used as the reagents 16. Alternatively, when the marking bodies 15a are enzymes which catalyze the color forming reaction, the reagents 16 need to include pigments.

Subsequently, a concentration of the antigens contained in the specimen solution 14a can be measured in such a manner that a difference in intensity between optical detection signals from the light receiving element 8 of FIG. 1 is measured. Specifically, in FIG. 1, a laser light from the light source 7 is input from the grating 2a into the optical waveguide 3, and is propagated through the optical waveguide 3 so as to generate evanescent light near the surface of the sensing area 101. In this situation, as illustrated in FIG. 17A, immediately after a mixture dispersion liquid of a specimen solution and the magnetic fine particles 9 is introduced into the reaction region 102 located on the sensing area 101, as illustrated in FIG. 17B, the magnetic fine particles 9 are settled so as to reach the vicinity of the surface of the optical waveguide 3 i.e. the region where the evanescent light is present.

Since the magnetic fine particles 9 contribute to absorbing or scattering of evanescent light, the intensity of a reflected light is attenuated. As a result, when the laser light which is output from the grating 2b is received by the light receiving element 8, the intensity of the output laser light decreases with elapse of time due to the influence of the magnetic fine particles 9 fixed to the optical waveguide 3. Subsequently, as illustrated in FIG. 17C, the magnetic fine particles 9 which are not absorbed to the optical waveguide 3 are moved by the magnetic field applying unit 10 so as to reach the outside of the region where the evanescent light is present, and the light receiving intensity is recovered to a predetermined value.

In this situation, as illustrated in FIG. 17D, when the reagents 16 are introduced into the reaction region 102 on the sensing area 101, marking bodies 15a fixed to the magnetic fine particles 9 illustrated in FIGS. 15 and 16 react with the reagents 16 so that a color forming reaction occurs. Since the light is absorbed by the color forming reaction, the intensity of the reflected light is further attenuated. The light receiving intensity at this time is compared with that in the state of FIG. 17A, i.e., a state immediately after the mixture dispersion liquid is introduced, and can be numerically shown as a reduction rate, for example.

The intensity reduction rate of the laser light which is received by the light receiving element 8 is dependent on the amount of the magnetic fine particles 9 which are mainly bonded to the surface of the optical waveguide 3 by the antigen-antibody reaction, and the color forming amount of the marking bodies 15a and the reagents 16. The intensity reduction rate of the laser light is proportional to the concentration of the antigens contained in the specimen solution involving with antigen-antibody reaction.

The curve which indicates a change in intensity of the laser light with elapse of time is obtained in advance by using a specimen solution having a known concentration of antigens. Furthermore, based on the curve, a laser intensity reduction rate at a predetermined time after application of the magnetic field is obtained, and a calibration curve indicating a relation between the concentration of the antigens and the laser intensity reduction rate is created.

Subsequently, a laser intensity reduction rate at a predetermined time is obtained from the curve which indicates change in laser light intensity at a predetermined time, using a specimen solution having an unknown concentration of antigens. The concentration of the antigens contained in the specimen solution can be measured by the combination of the laser light intensity reduction rate and the calibration curve.

Hereinafter, a specific example of the measuring method using the measuring system of the embodiment will be described. The specific numerical values or materials below are merely examples, and the example is not limited to those numerical values or materials.

A substrate 1 is prepared. The substrate 1 is formed of alkali-free glass so as to have a thickness of 50 nm and has a refractive index of 1.52. A titanium oxide film having a refractive index of 2.2 to 2.4 is formed on the substrate 1 by sputtering. Gratings 2a, 2b are formed by lithography and dry-etching of the titanium oxide film. A UV-curable acrylate resin film having a thickness of 10 μm is formed on the substrate 1, on which the gratings 2a, 2b are previously provided, by spin-coating and UV-irradiation. As a result, an optical waveguide layer 3 is formed. The refractive index of the optical waveguide layer 3 is 1.58 after curing.

A protective film 4 serving as a low refractive resin film is formed on a surface of the optical waveguide 3 including a region above the gratings 2a, 2b so as to surround a region corresponding to the sensing area 101 to which the antibodies are fixed. The refractive index of the dried protective film 4 is 1.34. A resinous frame 5 is fixed to the protective film 4 by a double coated tape so as to form a liquid storage for holding a specimen solution. Primary antibodies 6, as subject substances to be measured, are fixed to a surface of a region which is not covered with the protective film and is located between the gratings 2a, 2b, by a covalent binding method.

Rat insulin is used as the subject substances, and anti-rat insulin antibodies are used as the primary antibodies which are fixed to the surface of the optical waveguide 3. Furthermore, dispersion liquid is separately prepared in which anti-rat insulin antibodies as secondary antibodies and TMBZ which includes color forming pigments as marking bodies 15a are fixed to magnetic fine particles 9 having a mean diameter of 1.1 µm.

Subsequently, a light having a central wavelength of 635 nm from the light emitting diode 7 is input from the grating 2a, and the intensity of the light which is output from the grating 2b is measured by the photo diode 8. During this measurement, a specimen solution and the dispersion liquid of the magnetic fine particles 9 are mixed, and the mixture liquid is introduced into the reaction region 102 on the sensing area 101 (the inside of the frame 5). Furthermore, the measurement is performed according to the measurement sequence described by referring to FIGS. 17A to 17D.

According to the above measurement of the embodiment, since the light is absorbed by a color forming reaction of the marking bodies 16 in addition to absorbing and the scattering of the light using the magnetic fine particles 9 having a configuration of the magnetic fine particle 9a or 9B, it is possible to improve the sensitivity in detection of the subject substances.

Furthermore, when the specimen solution which includes the magnetic fine particles 9 to which the second substances 13 (the secondary antibodies) and the plural marking bodies 16 are fixed is introduced into the reaction region 102 before the reaction of the pigments, it is possible to cause plural color forming reactions by each reaction of a pair of antigen and antibody. Introduction of such a specimen solution allows the color forming amount caused by each reaction of a pair of antigen and antibody to increase. Accordingly, even the concentration of the subject substances is extremely low, color forming reaction can easily occur and the quantification can be performed with high sensitivity.

According to the above measurement of the embodiment, when the magnetic field is applied to the magnetic fine particles in a direction different from the settling direction, it is possible to move the magnetic fine particles, which are absorbed to the optical waveguide without using an antigen-antibody reaction and can cause noise in the measurement, from the optical waveguide. Accordingly, it is possible to measure the absorbency caused only by the magnetic fine particles bonded to the surface of the optical waveguide through the antigens by an antigen-antibody reaction and to reduce measurement error.

According to the embodiment, the subject substances 14 are measured by the evanescent light which is obtained in such a manner that the laser light is input into the optical waveguide 3 using the optical waveguide 3 of the optical waveguide type sensor chip 100. Thus, a distance, which is necessary for separating the magnetic fine particles from the surface of the optical waveguide to the extent that the measurement is not affected, can be shortened. As a result, the time which is necessary to separate the magnetic fine particles from the surface of the optical waveguide by the magnetic field in the upward direction can be shortened. Alternatively, it is possible to separate the magnetic fine particles 9 from the surface of the optical waveguide 3 to the extent that the measurement is not affected by using a magnetic field having a smaller strength.

Hereinafter, a measuring system and a measuring method using an optical waveguide, an optical waveguide type sensor chip, and magnetic fine particles according to a fifth embodiment will be described. The measuring system of the embodiment has the same configuration as that of the measuring system illustrated in FIG. 6 except for the configuration of magnetic fine particles 9. In the embodiment, the magnetic fine particle 9a, 9b illustrated in FIGS. 15 and 16 are used as the magnetic fine particles 9.

The method of measuring subject substances using the measuring system will be described by referring to FIGS. 18A to 18D. The steps illustrated in FIGS. 18A, 18C, and 18D are the same as those of FIGS. 17A, 17C, and 17D, respectively. The step of FIG. 18B will be described below.

In the step of FIG. 18A corresponding to FIG. 17A, a specimen solution 14a is introduced into the optical waveguide 3 where the magnetic fine particles 9 having a structure of the magnetic fine particle 9a or 9b are dispersed and held, and the magnetic fine particles 9 are dispersed again.

Subsequently, in the step of FIG. 18B, a magnetic field is applied by the magnetic field applying unit 11 of FIG. 6 as depicted by an arrow in a settling direction i.e. a downward direction of FIG. 6 when seen from the magnetic fine particles 9 having a configuration of the magnetic fine particle 9a or 9b. By application of the magnetic field, the magnetic fine particles 9 are attracted toward the optical waveguide 3. At this time, first substances 6 (primary antibodies) fixed to a surface of the optical waveguide 3 and second substances 13 (secondary antibodies) fixed to the magnetic fine particles 9 are bonded through the subject substances (the antigens) by an antigen-antibody reaction. Accordingly, the magnetic fine particles 9 are fixed to the surfaces of the optical waveguide 3.

Subsequently, as depicted by an arrow of FIG. 17C, a magnetic field is applied in a direction (an upward direction) different from the settling direction when seen from the magnetic fine particles 9, and the magnetic fine particles 9 absorbed to the surface of the optical waveguide 3 without using the subject substances 14 and the antigen-antibody reaction, are moved in a direction (the upward direction) different from the settling direction so as to be eliminated from the surface of the optical waveguide 3. Furthermore, as illustrated in FIG. 17D, reagents 16, which react with marking bodies 15 so as to cause a color forming reaction, are introduced into the reaction region 102. A concentration of the antigens contained in the specimen solution 14a can be measured in such a manner that a difference in intensity between optical detection signals from the light receiving element 8 of FIG. 6 is measured.

In the above measuring method, after the reagents 16 are introduced in the step of FIG. 18D, application of a magnetic field in the downward direction illustrated in FIG. 18B and application of a magnetic field in the upward direction illustrated in FIG. 18C may be alternately repeated.

When the magnetic fine particles 9 are attracted toward the optical waveguide 3 by application of the magnetic field in the downward direction as illustrated in FIG. 18B, part of the subject substances 14 remain in the specimen solution 14a, in a state that the part of the substances are not bonded to any one of the first substances 6 (the primary antibodies) or the second substances 13 (the secondary antibodies), or in a state that the part of the substances are bonded to the second substances 13 (the secondary antibodies) fixed to the magnetic fine particles but are not honed to the first substances 6 (the primary antibodies) fixed to the surface of the optical waveguide 3. Furthermore, the magnetic fine particles which are non-specifically absorbed to the surface of the optical waveguide 3 are present on the surface.

In order to prevent such a measurement of the magnetic fine particles, as illustrated in FIG. 18C, a magnetic field having an intensity, by which the magnetic fine particles 9 bonded by an antigen-antibody reaction are not separated, is applied, and the magnetic fine particles which are not bonded by an antigen-antibody reaction are moved in a direction different from the direction toward the optical waveguide 3.

Then, as illustrated in FIG. 18D, when the reagents 16 are introduced into the reaction region 102 provided on the sensing area 101, the marking bodies 15a fixed to the magnetic fine particles 9 react with the reagents 16 so that a color forming reaction occurs.

Further, as illustrated in FIG. 18B, when a magnetic field is applied in the direction toward the optical waveguide 3 so that the magnetic fine particles not bonded by an antigen-antibody reaction are attracted, the subject substances or the subject substances bonded to the second substances 13 (the secondary antibodies) fixed to the magnetic fine particles 9 are newly bonded to the first substances 6 (the primary antibodies) fixed to the surface of the optical waveguide 3.

Such steps are repeated so that the number of the magnetic fine particles which do not contribute to the antigen-antibody reaction can be decreased, and the number of the magnetic fine particles bonded to the surface of the optical waveguide 3 by the antigen-antibody reaction can be increased. Further, the magnetic fine particles 9 move upward and downward so as to be mixed with the reagents 16, and the color forming reaction of the marking bodies 15a fixed to the magnetic fine particles 9 and the reagents 16 is promoted. As a result, the S/N ratio can be improved.

According to the embodiment, when the magnetic field is applied from the second magnetic field applying unit 11 to the magnetic fine particles 9, the magnetic fine particles 9 can be attracted toward the optical waveguide 3. Since the magnetic fine particles 9 can be easily bonded to the surface of the optical waveguide by such an attraction, the sensitivity in detection of the subject substances can be improved.

In particular, when the magnetic fine particles 9 are attracted in the direction of the optical waveguide 3 immediately after the magnetic fine particles 9 and the specimen solution are introduced into the reaction region 102, it is possible to reduce the time necessary for natural settling of the magnetic fine particles 9 and to perform the measurement in a short time. Bonding between the magnetic fine particles 9 and the surface of the optical waveguide 3 can be promoted, before reaction or aggregation of the magnetic fine particles 9 with each other advances. As a result, since it is possible to further improve the rate of the subject substances contributing to bonding between the magnetic fine particles 9 and the surface of the optical waveguide 3, it is possible to obtain higher sensitivity in measurement.

Furthermore, when the magnetic fine particles 9 are moved using both or any one of the first magnetic field applying unit 10 and the second magnetic field applying unit 11, the specimen solution and the magnetic fine particles 9 can be mixed. The mixing allows the antigen-antibody reaction of the subject substances 14 (the antigens) contained in the specimen solution and the magnetic fine particles 9 to be promoted to obtain the higher sensitivity of detection in a shorter time.

In particular, after the reagents 16 are introduced, application of the magnetic field in the upward direction using the first magnetic field applying unit 10 and application of the magnetic field in the downward direction using the second magnetic field applying unit 11 are repeated so that the magnetic fine particles 9 can moved in a reciprocating manner. As a result, the magnetic fine particles are further mixed. By the mixing, the color forming reaction between the marking bodies 15a fixed to the magnetic fine particles 9 and the reagents 16 are promoted, and the color forming amount increases. Accordingly, the measurement can be performed with high precision even when the subject substances 14 are at a low concentration.

In the measurement according to the embodiment, since the magnetic fine particles 9 can be mixed using a magnetic field, a mixing operation by hand or a mixing mechanism having a pump is not needed so that a measuring system which is easily operated and is small in size can be realized. For example, when application of the magnetic field is automatically performed, the measurer can perform the measurement only by two operations by which a specimen solution and reagents are introduced into the measuring system.

Hereinafter, a measuring system and a measuring method using an optical waveguide, an optical waveguide type sensor chip, and magnetic fine particles according to a sixth embodiment will be described. In the measurements performed using the fourth and fifth embodiments, an antibody measuring method which is generally called as a sandwich method is used. In the measurement using the sixth embodiment, an antibody measuring method which is generally called as a competition method is used.

The optical waveguide type measuring system according to the embodiment is the same as the measuring system illustrated in FIG. 1 except for the configuration of the magnetic fine particles 9.

Figure 19:
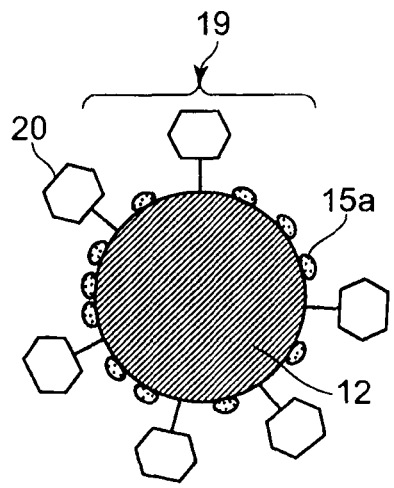
FIG. 19 is a schematic diagram illustrating still another example of the magnetic fine particles.

FIG. 19 is a diagram illustrating a magnetic fine particle 19 to be used in a sixth embodiment. The magnetic fine particle 19 is obtained in such a manner that third substances 20 (antigens to be measured) and marking bodies 15a are fixed to a surface of a fine particle 12. The materials and the sizes of the fine particle 12 and the marking bodies 15a are the same as those of the fine particles and the marking bodies used in the first and fourth embodiments. The third substances 20 have a property of bonding to the first substances (the primary antibodies) fixed to the optical waveguide 3 by a specific reaction. For example, the same substances as the antigens that are the subject substances 14 contained in the specimen solution used in the first and fourth embodiments can be employed as the third substances 20.

FIGS. 20A to 20F are diagrams illustrating steps of a method of measuring subject substances to be measured contained in a specimen solution using a measuring system according to the embodiment.

Figure 20A:
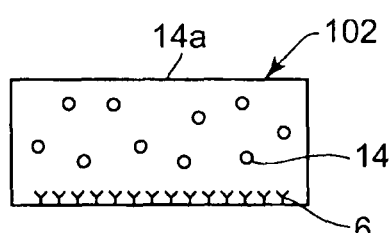
FIGS. 20A to 20F are diagrams illustrating steps of another method of measuring subject substances to be measured contained in a specimen solution.
Figure 20B:
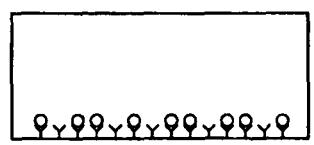

Magnetic fine particles 19 as shown illustrated in FIG. 19 are prepared. Subsequently, as illustrated in FIG. 20A, a specimen solution 14a which contains subject substances 14 (antigens) is introduced into the reaction region 102 provided on the optical waveguide 3. Then, as illustrated in FIG. 20B, the subject substances 14 contained in the specimen solution 14a are bonded to first substances 6 (primary antibodies) fixed to a surface of the optical waveguide 3.

Figure 20C:
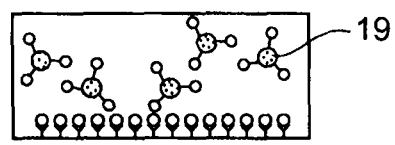
Figure 20D:
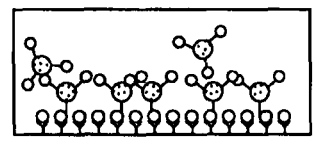

As illustrated in FIG. 20C, a solution which contains the magnetic fine particles 19 is introduced into the reaction region 102. Then, as illustrated in FIG. 20D, the magnetic fine particles 19 is settled to the surface of the optical waveguide 3 by their own weight. At this time, part of the first substances 6 (the primary antibodies), which are fixed to the surface of the optical waveguide 3 and are not bonded by the step of FIG. 18B, are bonded by an antigen-antibody reaction to the magnetic fine particles 19 through the third substances 20 (the antigens to be measured) which are fixed to the magnetic fine particles 19. Accordingly, the magnetic fine particles 19 are fixed to the surface of the optical waveguide 3.

Figure 20E:
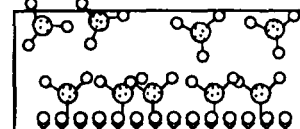

Subsequently, as depicted by an arrow of FIG. 20E, a magnetic field is applied in a direction different from a settling direction, for example, an upward direction when seen from the magnetic fine particles 19. A application of the magnetic field moves the magnetic fine particles, which are not bonded to a surface of the optical waveguide 3, in a direction (for example, the upward direction) different from the settling direction, so as to be eliminated from a surface region of the optical waveguide 3.

Figure 20F:
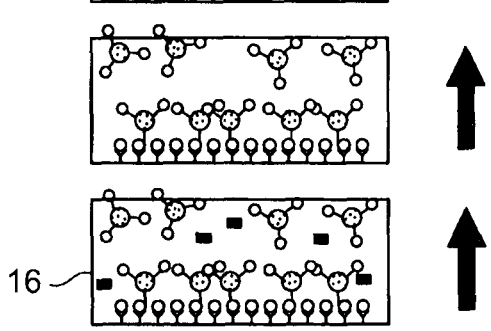

As illustrated in FIG. 20F, reagents 16 which form color through the reaction with the marking bodies 15a is introduced into the specimen solution 14a. Such an introduction may be performed by dripping or inflowing. In this case, in order to prevent the magnetic fine particles 9 from being naturally settled, it is desirable that the reagents 16 are introduced while the magnetic field is applied in a direction (for example, the upward direction) different from the settling direction when seen from the magnetic fine particles 9. For example, when the marking bodies 15a are TMBZ as pigments, a mixture solution of peroxidase and hydrogen peroxide, which is capable of forming color through reaction with TMBZ, can be used as the reagents 16. Alternatively, when the marking bodies 15a are enzymes which catalyze the color forming reaction, the reagents 16 need to include pigments.

Subsequently, similarly to the measuring method using the measuring system of the first embodiment, a difference in intensity between optical detection signals form the light receiving element 8 is measured. In the measurement according to the embodiment, since the magnetic fine particles 19 are bonded to the first substances 6 (the primary antibodies), to which the subject substances 14 (the antigens) are not absorbed by the antigen-antibody reaction, so that the color forming reaction occurs. As a result, the amount of the primary antibodies which do not cause the antigen-antibody reaction is measured. In the measurement of the embodiment, in contrast with the measurements according to the fourth and fifth embodiments, when the number of the subject substances 14 (the antigens) is small, the color forming amount increases so that the difference in signal intensity increases. Furthermore, when the number of the subject substances 14 (the antigens) is large, the color forming amount decreases so that the difference in signal intensity decreases. In this way, it is possible to measure the concentration of the antigens contained in the specimen solution with high precision.

Even when the magnetic fine particles 19 illustrated in FIG. 19 are used in the measuring system of the second embodiment illustrated in FIG. 6, the same measurement as that according to the measuring system of the sixth embodiment can be performed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Furthermore, a combination of the embodiments may be implemented.

What is claimed is:

1. A measuring system which uses an optical waveguide comprising:
    an optical waveguide having a sensing area to which first substances having a property of specifically bonding to subject substances to be measured are fixed;
    magnetic fine particles to which second substances having a property of specifically bonding to the subject substances are fixed;
    a magnetic field applying unit to generate a magnetic field for moving the magnetic fine particles, the magnetic field applying unit including a first magnetic field applying unit which applies a magnetic field in a direction for moving magnetic fine particles which are not combined with a subject substance at the sensing area further away from the optical waveguide without separating magnetic fine particles which are combined with a subject substance at the sensing area;
    a light source to input a light into the optical waveguide; and
    a light receiving element to receive the light output from the optical waveguide,
    wherein the magnetic field applying unit includes a core and a coil provided around the core,
    wherein an intensity of the light output from the waveguide is related to an amount of the magnetic fine particles combined with a subject substance, and
    wherein the core includes a plurality of core portions, a connection portion mechanically and magnetically connects first end portions of the core portions opposite to second end portions on an side of the sensing area, and a gap is provided between the second end portions.

2. The measuring system according to claim 1, wherein the sides of the second end portion facing the gap are parallel to a direction in which the light is propagated inside the optical waveguide.

3. The measuring system according to claim 1, wherein, in the direction in which the light is propagated inside the optical waveguide, each length of the end surfaces of the second end portion is equal to or longer than the length of the sensing area.

4. The measuring system according to claim 1, wherein the second portions of the core portions are inclined in a direction in which the end portions are close to each other.

5. The measuring system according to claim 1, wherein each part of the core portions are formed so that the cross-sectional area of the part becomes smaller as the part is closer to the sensing area.

6. The measuring system according to claim 1, wherein the end surfaces of the second portions on the side of the sensing area are flat.

7. A measuring system which uses an optical waveguide comprising:
    an optical waveguide having a sensing area to which first substances having a property of specifically bonding to subject substances to be measured are fixed;
    magnetic fine particles to which second substances having a property of specifically bonding to the subject substances are fixed;
    a magnetic field applying unit to generate a magnetic field for moving the magnetic fine particles, the magnetic field applying unit including a first magnetic field applying unit which applies a magnetic field in a direction for moving magnetic fine particles which are not combined with a subject substance at the sensing area further away from the optical waveguide without separating magnetic fine particles which are combined with a subject substance at the sensing area;
    a light source to input a light into the optical waveguide; and
    a light receiving element to receive the light output from the optical waveguide,
    wherein the magnetic field applying unit includes a core and a coil provided around the core,
    wherein an intensity of the light output from the waveguide is related to an amount of the magnetic fine particles combined with a subject substance, and
    wherein the core has a structure in which plates coated with insulator and having a magnetic property are stacked in a direction parallel to the magnetic field.

8. The measuring system according to claim 1, wherein the core portions and the connection portion are separable from each other.

* * * * *